(12) United States Patent
Ang et al.

(10) Patent No.: US 9,958,465 B2
(45) Date of Patent: May 1, 2018

(54) DETECTION APPARATUS HAVING A MICROFLUOROMETER, A FLUIDIC SYSTEM, AND A FLOW CELL LATCH CLAMP MODULE

(71) Applicants: Illumina, Inc., San Diego, CA (US); Illumina Singapore Pte Ltd, Singapore (SG)

(72) Inventors: Beng Keong Ang, Singapore (SG); Heng Kuang Cheng, Singapore (SG); John M. Beierle, San Diego, CA (US); Bradley Kent Drews, San Diego, CA (US); David Kaplan, San Diego, CA (US)

(73) Assignees: ILLUMINA, INC., San Diego, CA (US); ILLUMINA SINGAPORE PTE LTD, Singapore (SG)

( * ) Notice: Subject to any disclaimer, the term of this patent is extended or adjusted under 35 U.S.C. 154(b) by 0 days. days.

(21) Appl. No.: 15/403,896

(22) Filed: Jan. 11, 2017

(65) Prior Publication Data
US 2017/0199210 A1    Jul. 13, 2017

Related U.S. Application Data

(60) Provisional application No. 62/277,065, filed on Jan. 11, 2016.

(51) Int. Cl.
*G01N 35/00*    (2006.01)
*G01N 35/04*    (2006.01)
(Continued)

(52) U.S. Cl.
CPC ... *G01N 35/00029* (2013.01); *G01N 21/6456* (2013.01); *G01N 35/0099* (2013.01);
(Continued)

(58) Field of Classification Search
CPC .................. G01N 21/6428; B01L 3/502715
See application file for complete search history.

(56) References Cited

U.S. PATENT DOCUMENTS

| 5,139,744 A | 8/1992 | Kowalski |
| 8,101,431 B2 | 1/2012 | McDevitt et al. |

(Continued)

FOREIGN PATENT DOCUMENTS

| AU | 2014259551 A1 | 11/2014 |
| DE | 202014006405 U1 * | 12/2014 |
| WO | 2015031596 A1 | 3/2015 |

OTHER PUBLICATIONS

International Search Report and Written Opinion dated Apr. 13, 2017, for corresponding PCT Application No. PCT/US2017/012822 filed Jan. 10, 2017 (15 pages).

*Primary Examiner* — P. Kathryn Wright
(74) *Attorney, Agent, or Firm* — Illumina, Inc.

(57) ABSTRACT

Detection apparatus includes a microfluorometer having an objective, an excitation radiation source, and a detector. The detection apparatus also includes a fluidic system for delivering reagents from a reagent cartridge to a flow cell. The fluidic system includes a manifold body having a plurality of fluidic channels configured for fluid communication between the reagent cartridge and the flow cell. The fluidic system also includes a plurality of reagent sippers. The fluidic system also includes a valve configured to mediate fluid between reagent reservoirs and the flow cell. The detection apparatus also includes a flow cell latch clamp module having a clamp cover for holding the flow cell. The objective is configured to direct excitation radiation from the radiation source to the flow cell and to direct emission from the flow cell to the detector. The microfluorometer is movable to acquire wide-field images of different areas of the flow cell.

17 Claims, 25 Drawing Sheets

(51) Int. Cl.
  *G01N 35/10*    (2006.01)
  *G01N 21/64*    (2006.01)
  *G01N 35/02*    (2006.01)

(52) U.S. Cl.
  CPC ......... *G01N 35/04* (2013.01); *G01N 35/1095* (2013.01); *G01N 35/021* (2013.01); *G01N 2021/6482* (2013.01); *G01N 2035/00158* (2013.01); *G01N 2035/00326* (2013.01); *G01N 2035/0465* (2013.01)

(56) References Cited

U.S. PATENT DOCUMENTS

| | | | |
|---|---|---|---|
| 8,105,849 B2 | 1/2012 | McDevitt et al. | |
| 8,241,573 B2 | 8/2012 | Banerjee et al. | |
| 8,323,900 B2 | 12/2012 | Handique et al. | |
| 8,778,849 B2 | 7/2014 | Bowen et al. | |
| 8,895,249 B2 | 11/2014 | Shen et al. | |
| 8,951,781 B2 | 2/2015 | Reed et al. | |
| 8,956,580 B2 | 2/2015 | Lai et al. | |
| 9,012,022 B2 | 4/2015 | George et al. | |
| 9,096,890 B2 | 8/2015 | Zhou et al. | |
| 9,102,979 B2 | 8/2015 | Zhou et al. | |
| 9,146,248 B2 | 9/2015 | Hagerott et al. | |
| 9,169,513 B2 | 10/2015 | Shen et al. | |
| 9,193,996 B2 | 11/2015 | Buermann et al. | |
| 9,193,998 B2 | 11/2015 | Khurana et al. | |
| 9,193,999 B2 | 11/2015 | Fabani et al. | |
| 9,279,154 B2 | 3/2016 | Previte et al. | |
| 9,410,663 B2 | 8/2016 | Wright et al. | |
| 9,410,977 B2 | 8/2016 | Stone et al. | |
| 9,444,880 B2 | 9/2016 | Dickinson et al. | |
| 9,453,613 B2 | 9/2016 | Wright et al. | |
| 9,498,778 B2 | 11/2016 | Corey et al. | |
| 9,512,422 B2 | 12/2016 | Barnard et al. | |
| 2008/0125330 A1 | 5/2008 | Cady et al. | |
| 2010/0192612 A1 | 8/2010 | Reed et al. | |
| 2011/0207621 A1 | 8/2011 | Montagu et al. | |
| 2012/0270305 A1* | 10/2012 | Reed | B01L 3/502715 435/287.2 |
| 2013/0260372 A1* | 10/2013 | Buermann | G01N 21/6428 435/6.1 |
| 2014/0248618 A1 | 9/2014 | Shaikh et al. | |
| 2014/0329694 A1 | 11/2014 | Buermann et al. | |
| 2015/0045234 A1* | 2/2015 | Stone | B01L 3/502738 506/2 |
| 2015/0141291 A1 | 5/2015 | Zhou et al. | |
| 2015/0346097 A1 | 12/2015 | Battrell et al. | |
| 2016/0023208 A1 | 1/2016 | Fisher et al. | |
| 2016/0319350 A1 | 11/2016 | Stone et al. | |

* cited by examiner

DETECTION APPARATUS HAVING A MICROFLUOROMETER, A FLUIDIC SYSTEM, AND A FLOW CELL LATCH CLAMP MODULE

CROSS-REFERENCE TO RELATED APPLICATION

The present application claims the benefit of U.S. Provisional Application No. 62/277,065, filed on Jan. 11, 2016, which is incorporated herein by reference in its entirety.

BACKGROUND

Embodiments of the present disclosure relate generally to apparatus and methods for fluidic manipulation and optical detection of samples, for example, in nucleic acid sequencing procedures.

Our genome provides a blue print for predicting many of our inherent predispositions such as our preferences, talents, susceptibility to disease and responsiveness to therapeutic drugs. An individual human genome contains a sequence of over 3 billion nucleotides. Differences in just a fraction of those nucleotides impart many of our unique characteristics. The research community is making impressive strides in unraveling the features that make up the blue print and with that a more complete understanding of how the information in each blue print relates to human health. However, our understanding is far from complete and this is hindering movement of the information from research labs to the clinic where the hope is that one day each of us will have a copy of our own personal genome so that we can sit down with our doctor to determine appropriate choices for a healthy lifestyle or a proper course of treatment.

The current bottleneck is a matter of throughput and scale. A fundamental component of unraveling the blue print for any given individual is to determine the exact sequence of the 3 billion nucleotides in their genome. Techniques are available to do this, but those techniques typically take many days and thousands upon thousands of dollars to perform. Furthermore, clinical relevance of any individual's genomic sequence is a matter of comparing unique features of their genomic sequence (i.e. their genotype) to reference genomes that are correlated with known characteristics (i.e. phenotypes). The issue of scale and throughput becomes evident when one considers that the reference genomes are created based on correlations of genotype to phenotype that arise from research studies that typically use thousands of individuals in order to be statistically valid. Thus, billions of nucleotides can eventually be sequenced for thousands of individuals to identify any clinically relevant genotype to phenotype correlation. Multiplied further by the number of diseases, drug responses, and other clinically relevant characteristics, the need for very inexpensive and rapid sequencing technologies becomes ever more apparent.

What is needed is a reduction in the cost of sequencing that drives large genetic correlation studies carried out by research scientists and that makes sequencing accessible in the clinical environment for the treatment of individual patients making life changing decisions. Embodiments of the invention set forth herein satisfy this need and provide other advantages as well.

BRIEF SUMMARY

Provided herein is a detection apparatus including a microfluorometer having an objective, an excitation radiation source, and a detector. The microfluorometer is configured for wide-field image detection. The detection apparatus also includes a fluidic system for delivering reagents from a reagent cartridge to a flow cell. The fluidic system includes a manifold body having a plurality of fluidic channels configured for fluid communication between the reagent cartridge and an inlet of the flow cell. The fluidic system also includes a plurality of reagent sippers extending downward from ports in the manifold body. Each of the reagent sippers is configured to be placed into a reagent reservoir of the reagent cartridge so that liquid reagent can be drawn from the reagent reservoir into the reagent sipper. The fluidic system also includes a valve configured to mediate fluid communication between the reagent reservoirs and the inlet of the flow cell. The fluidic channels fluidly connect the reagent sippers to the valve. The detection apparatus also includes a flow cell latch clamp module having a clamp cover for holding the flow cell. The objective is configured to direct excitation radiation from the radiation source to the flow cell and to direct emission from the flow cell to the detector. The microfluorometer is movable to acquire wide-field images of different areas of an inner surface of the flow cell.

In some aspects, the detection apparatus includes no more than a single microfluorometer. Optionally, the microfluorometer includes a beam splitter that is positioned to direct excitation radiation from the excitation radiation source to the objective and to direct emission radiation from the objective to the detector.

In some aspects, the microfluorometer is an integrated microfluorometer having a compact epifluorescent detection configuration.

In some aspects, the microfluorometer is movable to allow imaging of the flow cell that is larger than a field of view of the microfluorometer.

In some aspects, the detection apparatus also includes a housing and a screen presented on a front face of the housing. The screen functions as a graphical user interface.

In some aspects, the detection apparatus also includes a housing having cartridge receptacle for receiving the reagent cartridge.

In some aspects, the detection apparatus also includes a fluidics automation module including a lift assembly for raising and lowering the reagent cartridge.

In some aspects, the detection apparatus also includes a fluidics automation module including a belt assembly that moves the reagent cartridge during loading.

In some aspects, the detection apparatus also includes a fluidics automation module including a lift assembly for raising and lowering the reagent cartridge and a belt assembly that moves the reagent cartridge during loading.

In some aspects, the manifold body is formed from multiple layers of solid material bonded together.

In some aspects, the channels are formed in the solid material prior to bonding the multiple layers together.

In some aspects, the fluidic channels are housed entirely within the manifold body.

In some aspects, the manifold body has at least sixteen (16) ports that connect to respective reagent sippers.

In some aspects, the valve is configured with inlet ports that correspond to each of the ports of the fluidic channels and configured with a single common outlet port which fluidly connects to the flow cell.

In some aspects, the fluidic system has no more than one valve that mediates fluid communication between the reagent reservoirs and the flow cell.

In some aspects, each of the fluidic channels originates from a single port and connects to a corresponding port of the valve.

In some aspects, the manifold body has a single layer of fluidic channels.

In some aspects, the reagent sippers have distal ends that are configured to pierce a film or foil layer of the reagent cartridge.

In some aspects, the radiation source produces radiation at different wavelengths.

In some aspects, the detector is a complementary metal-oxide-semiconductor (CMOS) image sensor.

In some aspects, the microfluorometer is a component of an imaging module. The imaging module also includes the flow cell latch clamp module. Optionally, the imaging module also includes an XY stage in which an X-motor and a Y-motor provide movement of the X-stage and the Y-stage, respectively. Optionally, the X-motor moves a camera assembly along an X-axis. The camera assembly has the microfluorometer, wherein the Y-motor moves the flow cell latch clamp module along a Y-axis.

In some aspects, the detection apparatus also includes a fluidic device that includes a flow cell cartridge and the flow cell. The flow cell cartridge is configured to hold the flow cell and facilitate orienting the flow cell for an imaging session.

In some aspects, the fluidic device and the flow cell cartridge are removable such that the flow cell cartridge is removable from the flow cell latch clamp module by an individual or machine without damage to the fluidic device or the flow cell cartridge.

In some aspects, the flow cell cartridge is configured to be repeatedly inserted and removed into the flow cell latch clamp module without damaging the flow cell cartridge or rendering the flow cell cartridge unsuitable for its intended purpose.

In some aspects, the flow cell cartridge includes a housing and a cover member that is coupled to the housing of the flow cell cartridge. The cover member includes a gasket having inlet and outlet passages that are located proximate to one another. The clamp cover includes a cover manifold with inlet and outlet ports that are configured to mate with the inlet passage and the outlet passage of the gasket, respectively.

In some aspects, the flow cell latch clamp module includes a spring-loaded lever that biases the flow cell against dowel pins.

In some aspects, a field diameter for the microfluorometer is at least 0.5 mm. Optionally, a field diameter for the microfluorometer is at least 2 mm. Optionally, a field diameter for the microfluorometer is no larger than 5 mm.

In some aspects, a numerical aperture for the microfluorometer is at least 0.2. Optionally, a numerical aperture for the microfluorometer is no greater than 0.8. Optionally, a numerical aperture for the microfluorometer is no greater than 0.5.

In some aspects, the microfluorometer has a resolution that is sufficient to distinguish features separated by at most 100 μm.

In an embodiments, a sequencing system is provided that includes the detection apparatus set forth above and the reagent cartridge having the reagent reservoirs. The reagent reservoirs include sequencing reagents.

In some aspects, at least one of the reagent reservoirs include a nucleic acid sample.

In some aspects, the reagent cartridge is removable from the detection apparatus.

In some aspects, the sequencing system is configured to perform a sequencing-by-synthesis protocol.

Provided herein is a detection apparatus, comprising (a) a carriage comprising one or more microfluorometers, wherein each of the one or more microfluorometers comprises an objective configured for wide-field image detection, wherein the one or more microfluorometers is positioned to acquire a plurality of the wide-field from a different area of the common plane; (b) a translation stage configured to move the carriage in at least one direction parallel to the common plane; and (c) a fluidic system for delivering reagents from a reagent cartridge to a flow cell comprising: a reagent manifold comprising a plurality of channels configured for fluid communication between a reagent cartridge and an inlet of a flow cell; a plurality of reagent sippers extending downward from ports in the manifold, each of the reagent sippers configured to be placed into a reagent reservoir in a reagent cartridge so that liquid reagent can be drawn from the reagent reservoir into the sipper; at least one valve configured to mediate fluid communication between the reservoirs and the inlet of the flow cell. In certain embodiments, the apparatus comprises no more than a single microfluorometer.

This disclosure further provides a fluidic system for delivering reagents from a reagent cartridge to a flow cell comprising: a reagent manifold comprising a plurality of channels configured for fluid communication between a reagent cartridge and an inlet of a flow cell; a plurality of reagent sippers extending downward from ports in the manifold, each of the reagent sippers configured to be placed into a reagent reservoir in a reagent cartridge so that liquid reagent can be drawn from the reagent reservoir into the sipper; at least one valve configured to mediate fluid communication between the reservoirs and the inlet of the flow cell.

This disclosure further provides a sequencing system comprising: a detection apparatus as described above; and a nucleic acid sample disposed within a reagent cartridge wherein the reagent cartridge is removable from the detection apparatus.

This disclosure further provides a sequencing system comprising: a detection apparatus as described above; and a nucleic acid sample disposed within a flow cell; wherein the flow cell is removable from the detection apparatus.

This disclosure further provides a sequencing method that includes the steps of (a) providing a sequencing system comprising (i) a flow cell comprising an optically transparent surface, (ii) a nucleic acid sample, (iii) a plurality of reagents for a sequencing reaction, and (iv) a fluidic system for delivering the reagents to the flow cell; (b) providing a detection apparatus comprising (i) a single microfluorometer, wherein the microfluorometer comprises an objective configured for wide-field image detection in an image plane in x and y dimensions, and (ii) a sample stage; and (c) carrying out fluidic operations of a nucleic acid sequencing procedure in the cartridge and detection operations of the nucleic acid sequencing procedure in the detection apparatus, wherein (i) the reagents are delivered to the flow cell by the fluidic system, (ii) wide-field images of the nucleic acid features are detected by the microfluorometer.

The details of one or more embodiments are set forth in the accompanying drawings and the description below. Other features, objects, and advantages will be apparent from the description and drawings, and from the claims.

DETAILED DESCRIPTION

Figure 1A:
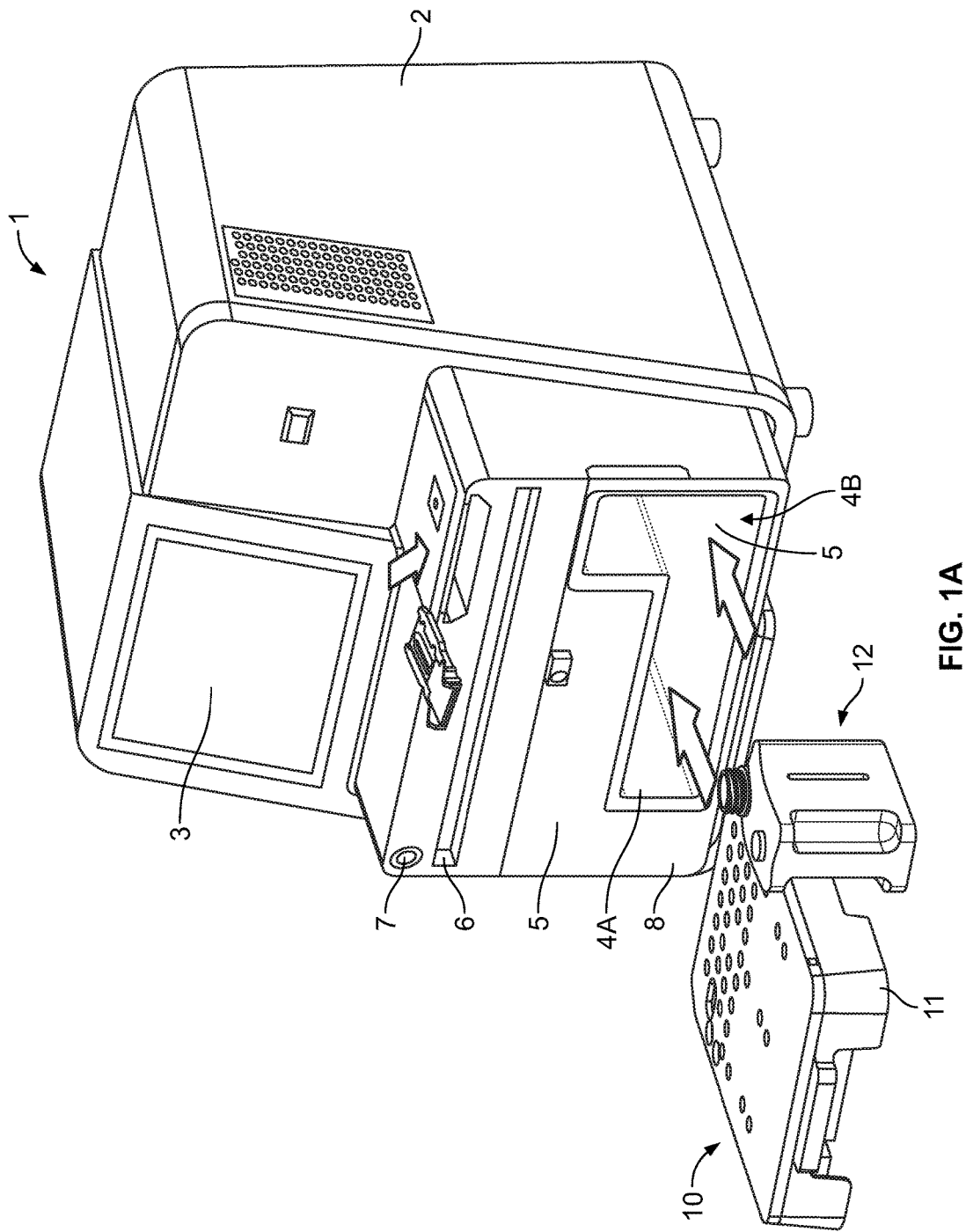
FIG. 1A shows an integrated optoelectronics and fluidic detection device useful for nucleic acid sequencing.

This disclosure provides methods and apparatus for high-resolution detection of planar areas such as those present on substrate surfaces. A particularly useful application is optically based imaging of a biological sample that is present on a surface. For example, the methods and apparatus set forth herein can be used to obtain images of nucleic acid features that are present in nucleic acid arrays, such as those used in nucleic acid sequencing applications. A variety of nucleic acid sequencing techniques that utilize optically detectable samples and/or reagents can be used. These techniques are particularly well suited to the methods and apparatus of the present disclosure and therefore highlight various advantages for particular embodiments of the invention. Some of those advantages are set forth below for purposes of illustration and, although nucleic acid sequencing applications are exemplified, the advantages can be extended to other applications as well.

In regard to some of the examples set forth herein, salient characteristics of many nucleic acid sequencing techniques are (1) the use of multicolor detection (e.g. often four different fluorophores are used, one for each of the different nucleotide types A, C, G and T (or U) present in nucleic acids), (2) distribution of large numbers of different fragments from a nucleic acid sample (e.g. fragments from a genome sample, RNA sample, or derivative thereof) onto the surface of an array and (3) repeated cycles of fluidic processing and imaging of the arrays. Embodiments of the methods and apparatus disclosed herein are particularly useful for nucleic acid sequencing because they can provide the capability of high resolution imaging of array surfaces in multiple colors and in multiple repetitions. For example, embodiments set forth herein allow an image of a surface to be obtained at a resolution that is in the range of hundreds, tens or even single digit microns. As such, nucleic acid features having nearest neighbor, average center-to-center spacing that is lower than 100 microns, 50 microns, 10 microns, 5 micron or fewer can be resolved. In particular embodiments, wide-field images of surfaces can be acquired, including for example, images that cover an area of 1 mm$^2$ or more of an array. The images can be acquired in multiple colors simultaneously or sequentially, for example, to identify fluorescent labels uniquely associated with different nucleotide types. Moreover, images can be acquired sequentially for multiple cycles of a sequencing technique. The images from a given area of the array can be reliably compared from each cycle to determine the sequence of color changes detected for each nucleic acid feature on the array. The sequence of color changes can in turn be used to infer the sequences of the nucleic acid fragments in each feature.

In particular embodiments, an apparatus of the present disclosure includes one or more microfluorometers. Each of the microfluorometers can include an excitation radiation source, a detector and an objective to form an integrated subunit of a read head. Other optical components can be present in each microfluorometer. For example a beam splitter can be present to provide for a compact epifluorescent detection configuration, whereby the beam splitter is positioned to direct excitation radiation from the excitation radiation source to the objective and to direct emission radiation from the objective to the detector.

An advantage of using an integrated microfluorometer design is that the microfluorometer can be conveniently moved, for example in a scanning operation, to allow imaging of a substrate that is larger than the field of view of the microfluorometer. In particular embodiments, a single microfluorometer can form a read head. In particular embodiments, several microfluorometers can be combined to form a read head. Various configurations for one or more read heads are set forth below and can be selected to suit a particular format for a substrate that is to be imaged, while maintaining relatively compact size for the overall read head. The relatively small size and low mass of the read head in several embodiments of the present disclosure results in relatively low inertia such that the read head comes to rest quickly after being moved, thereby favoring rapid scanning of a nucleic acid array or other substrate. In some cases, the microfluorometer can be affixed to a carriage such that they are not independently moveable in at least some dimensions during the course of an analytical application such as a nucleic acid sequencing run. The microfluorometer may, however, be independently actuated in the z dimension to provide for independent focus control. Reducing degrees of freedom between several different microfluorometers of an apparatus of the present disclosure provides for protection against loss of alignment during shipping, handling and use of the apparatus.

In some embodiments, multiple microfluorometers that are present in a read head or carriage can each have a dedicated autofocus module. Accordingly, each microfluorometer can be independently focused. In some embodiments, a particular autofocus modules in a read head, although dedicated to actuation of a particular microfluorometer, can nevertheless receive information from at least one other autofocus module in the read head and the information from that particular autofocus module and from the at least one other autofocus module can be used to determine an appropriate actuation to achieve desired focus for the particular microfluorometer. In this way focus for any given microfluorometer can be determined by consensus between two or more microfluorometers present in the same read head or carriage.

In particular embodiments, a sample that is to be detected can be provided to a detection chamber using a fluidic system as provided herein. Taking the more specific example of a nucleic acid sequencing application, the fluidic system can include a manifold assembly that can be placed into fluidic communication with one or more of reservoirs for holding sequencing reagents, reservoirs for holding sample preparation reagents, reservoirs for holding waste products generated during sequencing, and/or pumps, valves and other components capable of moving fluids through a flow cell.

In particular embodiments a fluidic system can be configured to allow re-use of one or more reagents. For example, the fluidic system can be configured to deliver a reagent to a flow cell, then remove the reagent from the flow cell, and then re-introduce the reagent to the flow cell. An advantage of re-using reagents is to reduce waste volume and reduce the cost of processes that utilize expensive reagents and/or reagents that are delivered at high concentrations (or in high amounts). Reagent re-use takes advantage of the understanding that depletion of reagent occurs only or primarily at the flow cell surface, and therefore a majority of the reagent goes unused and may be subject to re-use.

FIG. 1A shows an exemplary detection device 1 that exploits advantages of integrated optoelectronics and fluidic systems that are provided by several embodiments set forth herein. The exemplary detection device 1 includes a housing 2 that contains various fixed components including, for example, optical components, computational components, power source, fan and the like. A screen 3 present, for example, on the front face of the housing 2 functions as a graphical user interface that can provide various types of information such as operational status, status of an analytical procedure (e.g. a sequencing run) being carried out, status of data transfer to or from the detection device 1, instructions for use, warnings or the like. A cartridge receptacle 4A is also present on the front face of the housing 2. A waste reservoir receptacle 4B is also present on the front face of the housing 2. As shown, the cartridge receptacle 4A and waste reservoir receptacle 4B can be configured as a slot having a protective door 5. A status indicator 6, in the form of an indicator light on the frame of the cartridge receptacle in this example, is present and can be configured to indicate the presence or absence of a reagent cartridge in the detection device 1. For example the indicator light 6 can change from on to off or from one color to another to indicate presence or absence of a cartridge. A power control button 7 is present on the front face of the housing 2 in this example as is identifying indicia 8 such as the name of the manufacturer or instrument.

Also shown in FIG. 1A is an exemplary reagent cartridge 10 that can be used to provide a sample and reagents to the detection device 1. The reagent cartridge 10 includes a cartridge housing 11 that protects various fluidic components such as reservoirs, fluidic connections, and the like. A bar code or other machine readable indicia can optionally be present on the cartridge housing 11, for example, to provide sample tracking and management. Other indicia can also be present on the housing for convenient identification by a human user, for example, to identify the manufacturer, analytical analysis supported by the fluidic cartridge, lot number, expiration date, safety warnings and the like.

Also shown in FIG. 1A is a waste reservoir 12 that can be inserted into the waste reservoir receptacle 4B. The waste reservoir 12 is configured to receive waste fluid through an opening on the top of the reservoir.

The device shown in FIG. 1A is exemplary. Further exemplary embodiments of the methods and apparatus of the present disclosure that can be used alternatively or additionally to the example of FIG. 1A are set forth in further detail below.

Figure 1B:
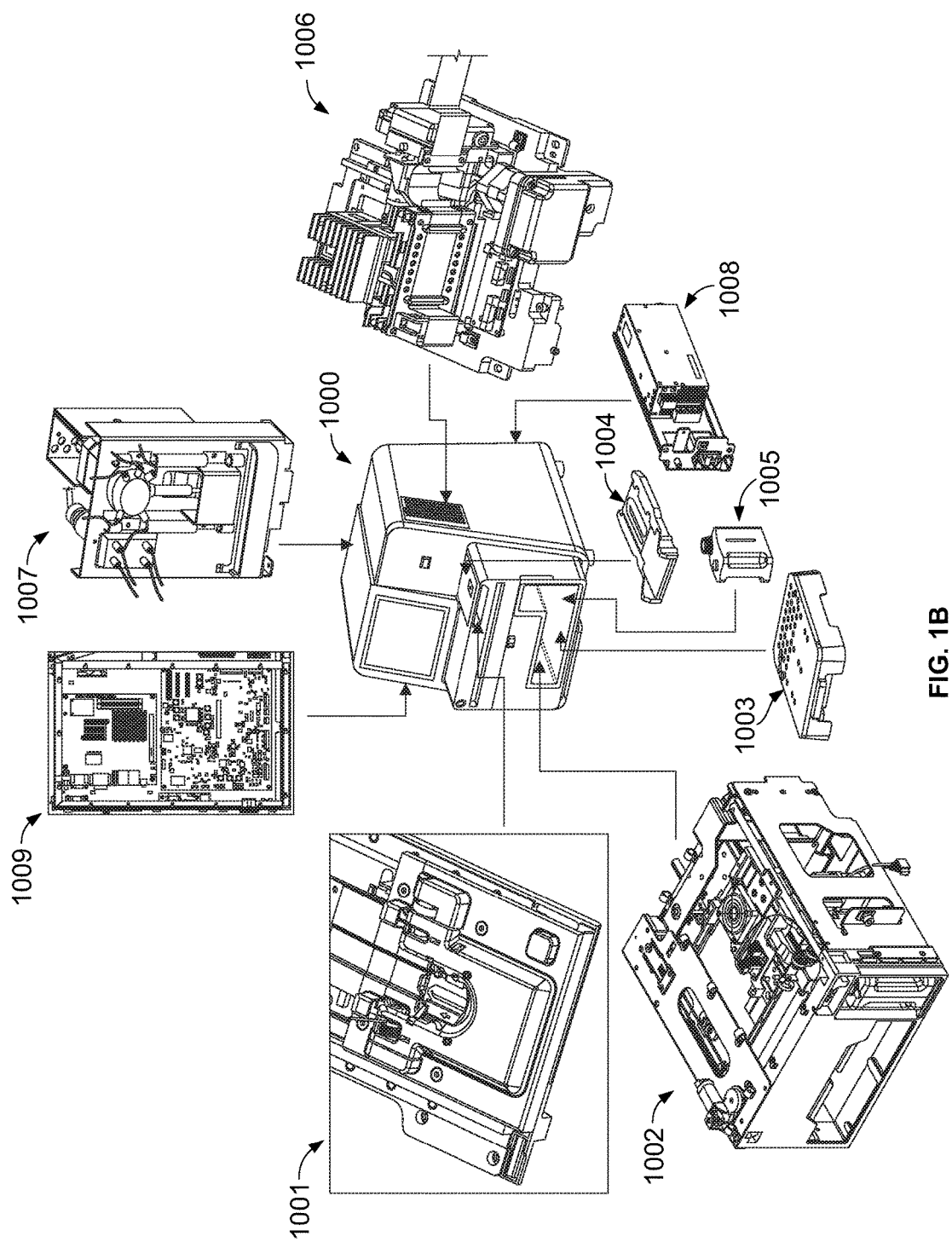
FIG. 1B shows an exploded view of several of the modules and systems that make up the integrated optoelectronics and fluidic detection device shown in FIG. 1A.
Figure 9:
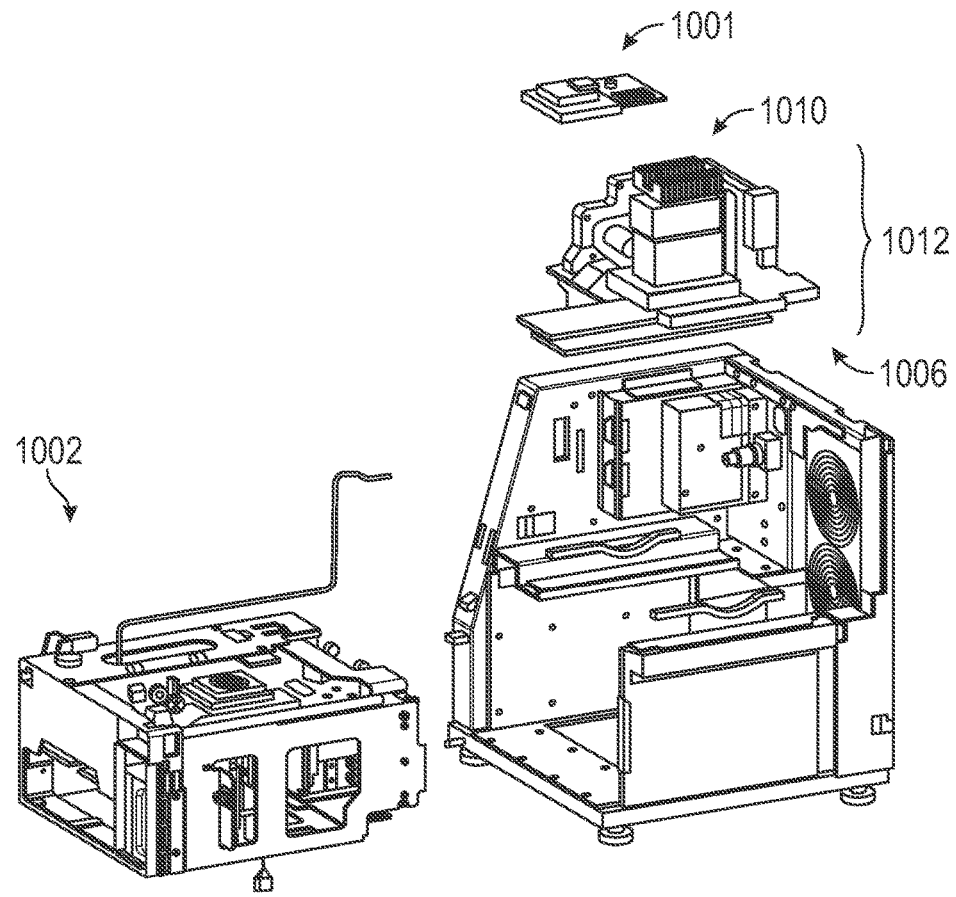
FIG. 9 is a partially exploded view of the device of FIG. 1 in accordance with an embodiment.

FIG. 1B shows components of the exemplary detection device or detection apparatus 1000, including a fluidic pump 1001 that is in fluid communication with a fluidics automation module (FAM) 1002. FAM 1002 is configured to be placed in fluid communication with reagent cartridge 1003, flow cell 1004 and waste reservoir 1005 so as to move liquid reagents from reagent cartridge 1003 onto flow cell 1004 and to waste reservoir 1005. Also shown in FIG. 1B is XY stage 1006, including flow cell latch clamp module 1001. Also shown in FIG. 1B is power supply unit 1008 and main printed circuit board (PCB) 1009. As shown in FIG. 9, the XY stage 1006 is configured to have an imaging module 1010 mounted thereon and the flow cell latch clamp module 1001. Also shown in FIG. 9, the detection apparatus 1000 may include a plurality of modular systems that are constructed as separate sub-systems that are then positioned within the housing. For example, the imaging module 1010 and the XY stage 1006 may form a first modular sub-system 1012. The flow cell clamp module 1001 may form a second modular sub-system. The fluidics automation module 1002 may form a third modular sub-system. In some embodiments, the flow cell clamp module 1001 may be removably coupled to the XY stage 1006 (or the first modular sub-system 1012). As such, the flow cell latch clamp module 1001 may be removed without separating the imaging module 1010 with respect to the XY stage 1006.

Figure 2A:
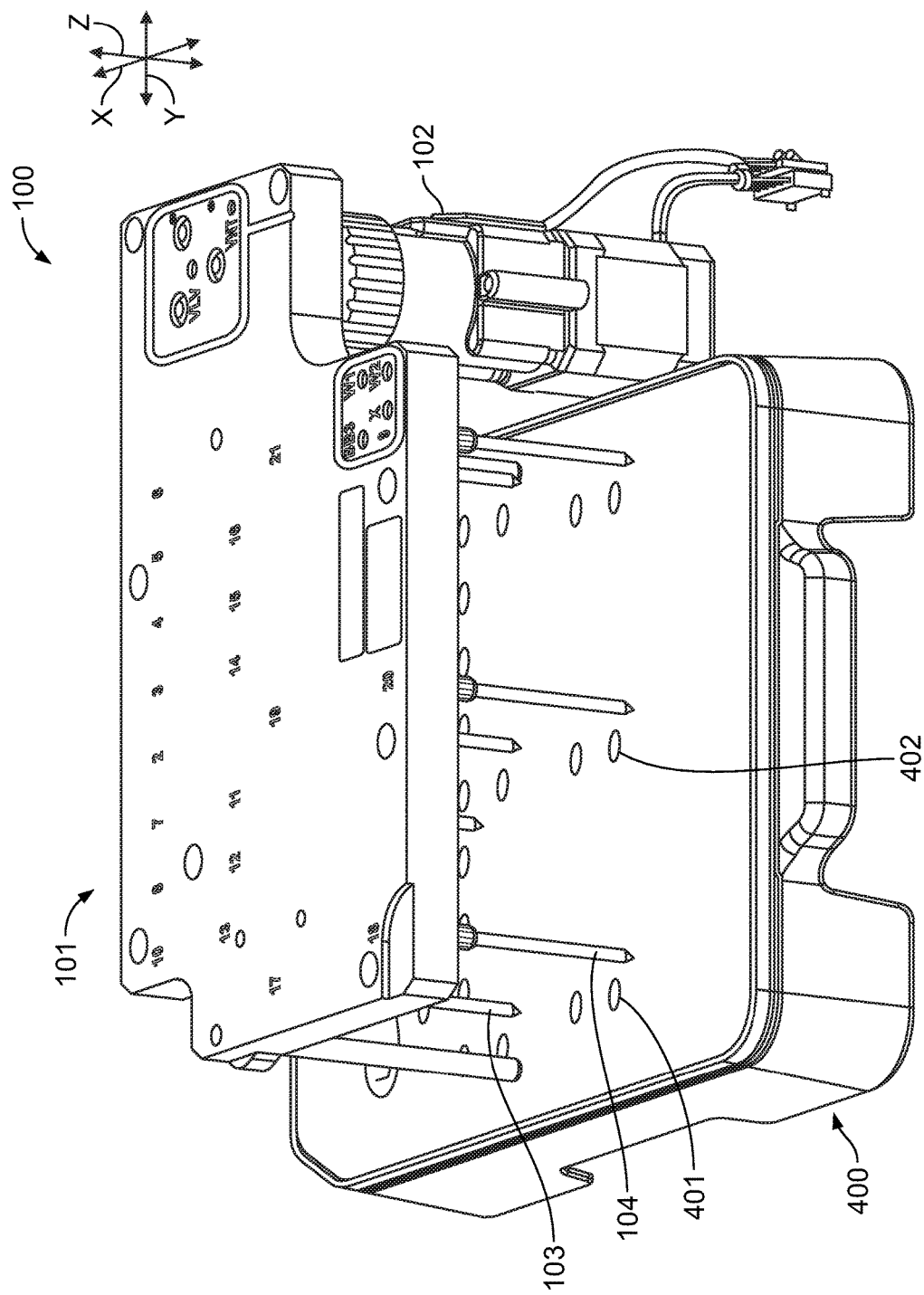
FIG. 2A shows a perspective view of a manifold assembly having reagent sippers, valve and alignment pins. It also shows a reagent cartridge.

FIG. 2A shows an exemplary fluidic system 100 having reagent sippers 103 and 104 and valves 102 that exploits advantages of fluidic systems that are provided by several embodiments set forth herein. The fluidic system 100 includes a manifold assembly 101 that contains various fixed components including, for example, reagent sippers, valves, channels, reservoirs and the like. A reagent cartridge 400 is present having reagent reservoirs 401 and 402 (hereinafter referred to as "wells") configured to simultaneously engage a set of reagent sippers 103 and 104 along a dimension z such that liquid reagent can be drawn from the reagent reservoirs into the sippers.

Figure 2B:
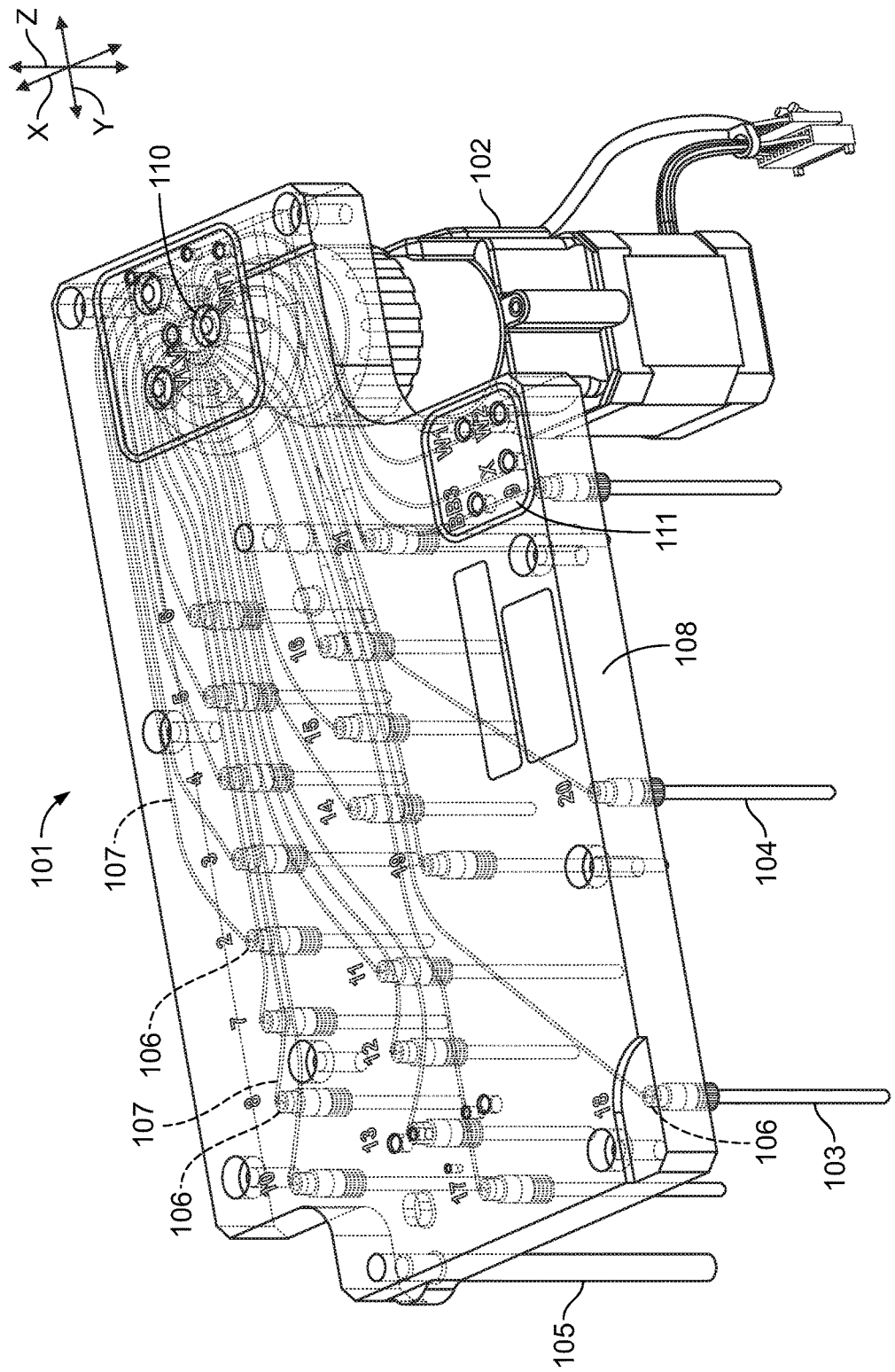
FIG. 2B shows a perspective view of a manifold assembly having reagent sippers, valve and alignment pins.

Shown in FIG. 2B is an exemplary manifold assembly 101 that can be used to provide liquid reagents from reagent reservoirs to a flow cell. The manifold assembly 101 includes reagent sippers 103 and 104 extending downward in a dimension z from ports 106 in the manifold. The reagent sippers 103 and 104 can be placed into one or more reagent reservoirs (not shown) in a reagent cartridge. The manifold body 108 also includes fluidic channels 107 fluidly connecting the reagent sipper 103 to a valve 102. The reagent sippers 103 and 104, the fluidic channels 107 and the valve 102 mediate fluid communication between the reagent reservoirs and a flow cell (not shown). Valves 102 and 109 may individually, or in conjunction, select reagent sippers 103 or 104, and through fluidic channels such as 107, mediate fluid communication between the reagent reservoirs and a flow cell (not shown).

Figure 2C:
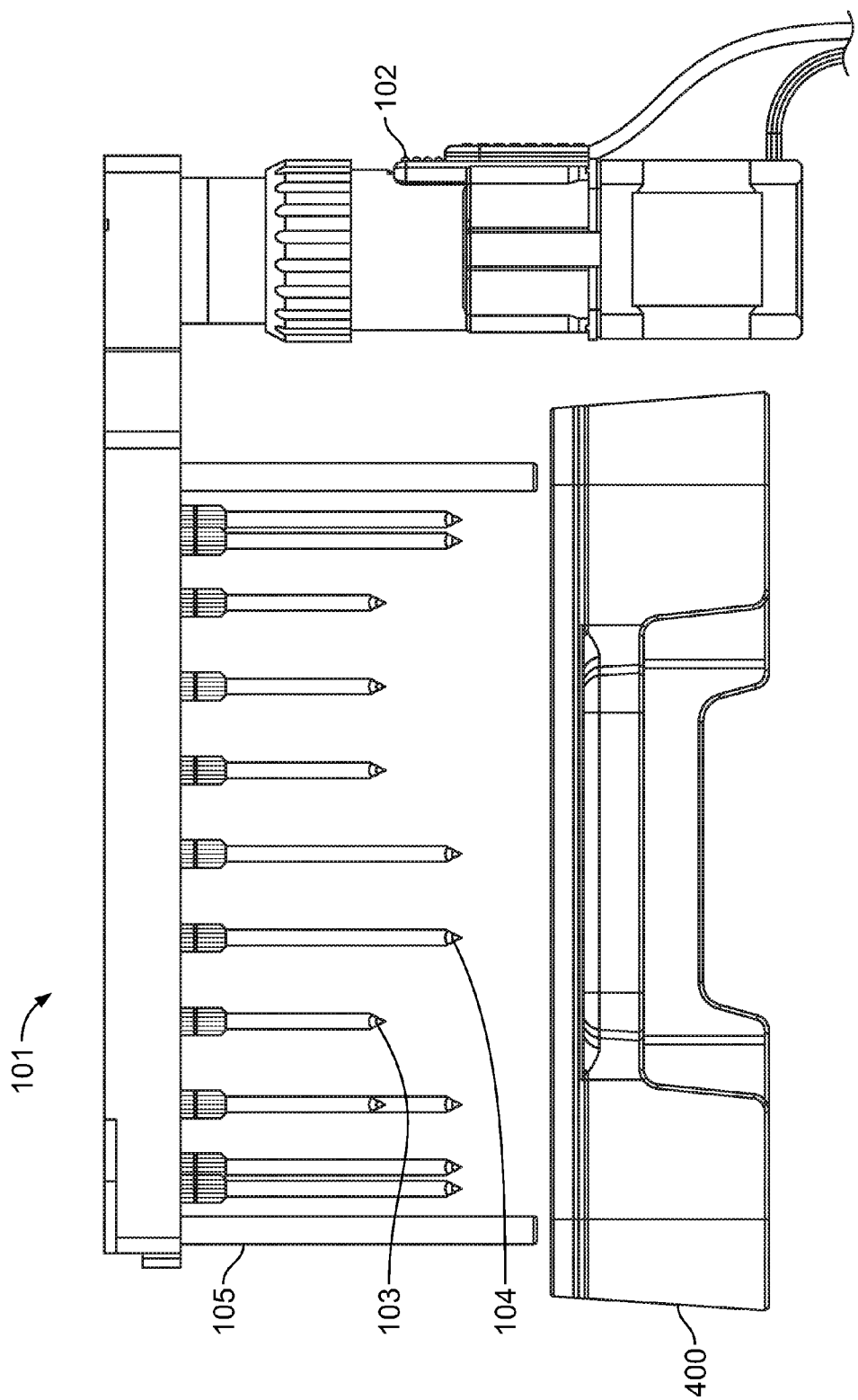
FIG. 2C shows a side view of a manifold assembly having reagent sippers of varying length, valve and alignment pins. It also shows a reagent cartridge.

FIG. 2C shows a side view of an exemplary fluidic system 100 having reagent sippers and valves. The manifold has alignment pins 105 protruding downward from the manifold in an axis parallel to the reagent sippers. The alignment pins 105 are longer along the z dimension compared to the reagent sippers, although in alternative embodiments they can also be of equal length or shorter. The alignment pins 105 are configured to engage with one or more corresponding interface slots on a reagent cartridge (not shown). The reagent sippers 103 and 104 are coupled to the manifold via ports 106 that are housed in a manifold body 108 of the manifold assembly 101. Reagent sippers 104 are longer in comparison to reagent sippers 103, in order to draw liquid from reagent reservoirs of varying depth that corresponds to the depth of the reagent sipper 103 or 104. In alternative embodiments, reagent sippers 103 and 104 can be of equal lengths, or may switch dominant lengths.

FIG. 2B shows a view of a manifold assembly 101 displaying one possible layout of fluidic channels 107 within the manifold body 108. Each of the fluidic channels 107 originates from a single port 106 and connects a corresponding port 106 to the valve 102. In some embodiments, certain channels can include a cache reservoir which has sufficient volume to allow a quantity of liquid reagent to flow from a flow cell (not shown) to the cache reservoir such that liquid reagent from the flow cell is not directed back to the reagent reservoir (not shown) after contacting the flow cell. Also shown in FIG. 2B are exemplary positions of one or more alignment pin 105. The manifold assembly shown in FIG. 2B also includes inlet ports 111 for shared buffers. Valve 102 is configured with inlet ports corresponding to each port 106, and with a common out port 110 which fluidly connect to a flow cell and a waste port which fluidly connect to a waste receptacle.

As demonstrated by the exemplary embodiments above, a fluidic system for delivering reagents from a reagent cartridge to a flow cell can include a reagent manifold comprising a manifold body having a plurality of channels configured for fluid communication between a reagent cartridge and an inlet of a flow cell. Use of a manifold body in fluidic systems provides several advantages over the use of tubing alone. For example, a manifold body with fixed fluidic channels reduces the likelihood of error during assembly, such as misplacement of tubing attachments, as well as over- or under-tightening of connections. In addition, a manifold body provides ease of maintenance, allowing, for example, quick replacement of an entire unit rather than time-intensive testing and replacement of individual lines.

The one or more of the channels of the manifold can include a fluidic track through a solid material. The track can be of any diameter to allow desired level of fluid transfer through the track. The track can have an inner diameter of, for example, less than 0.1 mm, 0.2 mm, 0.3 mm 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm or less than 10 mm in diameter. The track configuration can be, for example, straight or curved. Alternatively or additionally, the track can have a combination of curved portions and straight portions. The cross section of the track can be, for example, square, round, "D"-shaped, or any other shape that enables a desired level of fluid transfer through the track.

The channel between the sipper and the valve can be housed entirely within the manifold body 108. Alternatively or additionally, the channel can include one or more portions that are external to the manifold. For example, tubing such as, for example, flexible tubing can connect a portion of the fluidic track to another portion of the track on the manifold. Alternatively or additionally, flexible tubing can connect a flow cell to fixed fluidic components of the system, including, for example, pumps, valves, sensors and gauges. As an example, flexible tubing can be sued to connect a flow cell or a channel of the present system to a pump such as a syringe pump or a peristaltic pump.

The manifold body 108 can be, for example, made of any suitable solid material that is capable of supporting one or more channels therein. Thus, the manifold body 108 can be a resin such as polycarbonate, polyvinyl chloride, DELRIN® (Polyoxymethylene); HALAR®; PCTFE (PolyChloroTriFluoroEthylene); PEEK™ (Polyetheretherketone); PK (Polyketone); PERLAST®; Polyethylene; PPS (Polyphenylene Sulfide); Polypropylene; Polysulfone; FEP; PFA; High Purity PFA; RADEL® R; 316 Stainless Steel; TEFZEL® ETFE (Ethylene Tetrafluoroethylene); TPX® (Polymethylpentene); Titanium; UHMWPE (Ultra High Molecular Weight Polyethylene); ULTEM® (polyetherimide); VESPEL® or any other suitable solid material that is compatible with the solvents and fluids transported through the channels of the manifold in the embodiments presented herein. The manifold body can be formed from a single piece of material. Alternatively or additionally, the manifold body can be formed from multiple layers that are bonded together. Methods of bonding include, for example, the use of adhesives, gaskets, and diffusion bonding. The channels can be formed in the solid material by any suitable method. For example, channels can be drilled, etched or milled into the solid material. Channels can be formed in the solid material prior to bonding multiple layers together. Alternatively or additionally, channels can be formed after bonding layers together.

The manifold assemblies presented here are configured for delivery of liquid reagents from a reagent cartridge to a flow cell. Thus, the manifold can have any number of ports coupled to reagent sippers. More specifically, the number of ports can correspond to the number and configuration of reagent reservoirs in a reagent cartridge. In some embodiments, the manifold comprises at least 2, 3, 4, 5, 6, 7, 8, 9, 10, 11, 12, 13, 14, 15, 16, 17, 18, 19, 20, or at least 30 ports, each port configured to couple a reagent sipper to a channel in fluid communication with the at least one valve.

The fluidic systems presented herein can also include an array of sipper tubes extending downward along the z dimension from ports in the manifold body, each of the reagent sippers configured to be inserted into a reagent reservoir in a reagent cartridge so that liquid reagent can be drawn from the reagent reservoir into the sipper. The reagent sippers can comprise, for example, a tubular body with a proximal end and a distal end. The distal end can taper to a sharp tip that is configured to pierce a film or foil layer used as a seal over a reagent reservoir in a reagent cartridge. The reagent sippers can be provided with, for example, a single lumen running through the tubular body from the distal to the proximal end. The lumen can be configured to provide fluid communication between the reagent cartridge on one end of the sipper and the reagent manifold on the other end of the sipper. As shown in exemplary FIG. 2B, reagent sippers 103 and 104 are coupled to the manifold body 108 via ports 106 that are housed in the manifold body 108.

In some embodiments, as exemplified in FIG. 2C, a subset of the reagent sippers is of a length that is shorter than other reagent sippers. For example, the length of the subset can be at least 1, 1.2, 1.3, 1.4, 1.5, 1.6, 1.7, 1.8, 1.9, or at least 2.0 mm shorter than the other reagent sippers. The manifold and reagent sippers can be used in a device having an elevator mechanism configured to move a reagent cartridge bi-directionally along the z dimension such that the reagent sippers are inserted into corresponding wells or reservoirs in the reagent cartridge. In certain embodiments, the reagent wells may be covered with protective foils. Thus, an advantage of providing sippers of varying length is a reduction in the force required by the elevator mechanism to accommodate a foil-piercing force when a reagent cartridge is brought into contact with the piercing sippers. The difference in sipper length can advantageously correspond to the depth of reagent wells in a reagent cartridge, so that each sipper reaches a desired depth in its corresponding reagent well when the sippers and the cartridge are in a fully engaged position.

The sippers can be formed of any suitable material that allows fluid transfer through a lumen and which is compatible with the solvents and fluids transported through the channels of the manifold in the embodiments presented herein. The sippers can be formed from a single tube. Alternatively or additionally, one or more sippers can be made of multiple segments that together form a sipper of a desired length and diameter.

In some embodiments, at least one of the reagent sippers includes a compliant tip configured to flex when the tip impinges upon the bottom of a reagent well in a reagent cartridge. By flexing or deforming, a compliant tip allows the lumen of the sipper to more fully approach or even contact the bottom of the reagent well, thereby reducing or even eliminating the evacuation volume in the reagent well. A compliant tip can be especially advantageous for uptake of sample or reagents where small volumes are used, or in situations where it is desirable for uptake of most or all of the liquid in a reagent reservoir. The body of the sipper having a compliant tip can be made entirely of the same flexible material as the tip. Alternatively or additionally, the body of the sipper can be made of a distinct material than the tip. The compliant tip can be made of any suitable material such that the compliant tip may deform or yield when urged into contact with the bottom of a reagent reservoir. Some suitable materials include polymeric and/or synthetic foams, rubber, silicone and/or elastomers, including thermoplastic polymers such as polyurethane.

Figure 2D:
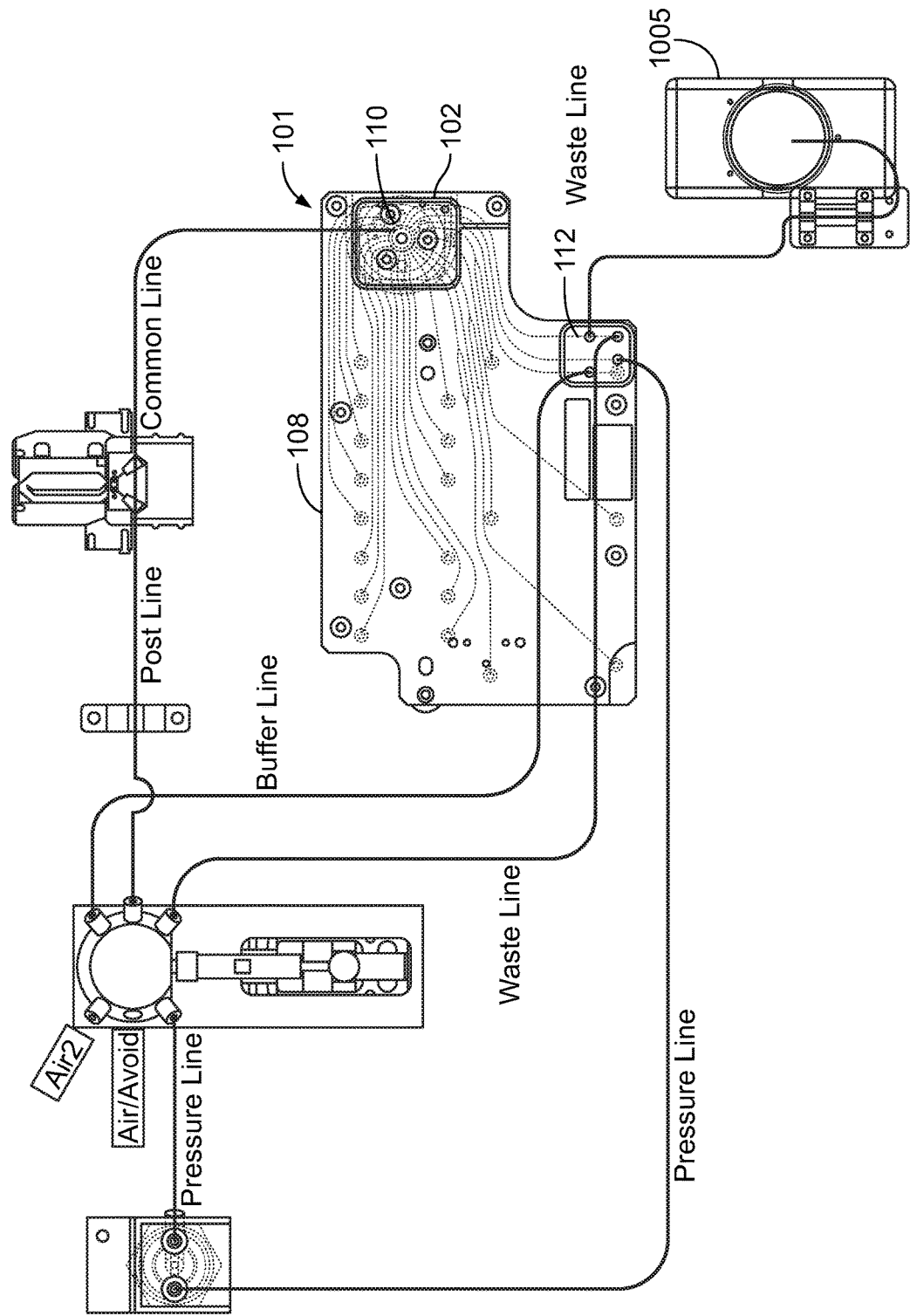
FIG. 2D shows a fluidics map for a fluidic system.

The fluidic systems presented herein may also include, for example, pumps and valves that are selectively operable for controlling fluid communication between the reservoirs and the inlet of the flow cell. As exemplified by the manifold assembly 101 shown in FIG. 2D, channel outlets on the manifold body 108 can be configured to connect with corresponding inlet ports on the valve 102 such that each fluidic channel 107 is in fluid communication with an inlet port on the valve 102. Thus, via the fluidic channels 107 of the manifold body 108, one or more or each of the inlet ports can be in fluid communication with a reagent sipper. The valve 102 can be configured with a common out port 110 which fluidly connects to an inlet of one or more lanes on a flow cell. Alternatively or additionally, the valve 102 can be configured with a waste port 112 fluidly connected to one or more waste reservoirs 1005.

The apparatuses shown in FIGS. 2A, 2B, 2C and 2D are exemplary. Further exemplary embodiments of the methods and apparatus of the present disclosure that can be used alternatively or additionally to the example of FIGS. 2A, 2B, 2C and 2D are set forth in further detail below.

Figure 3A:
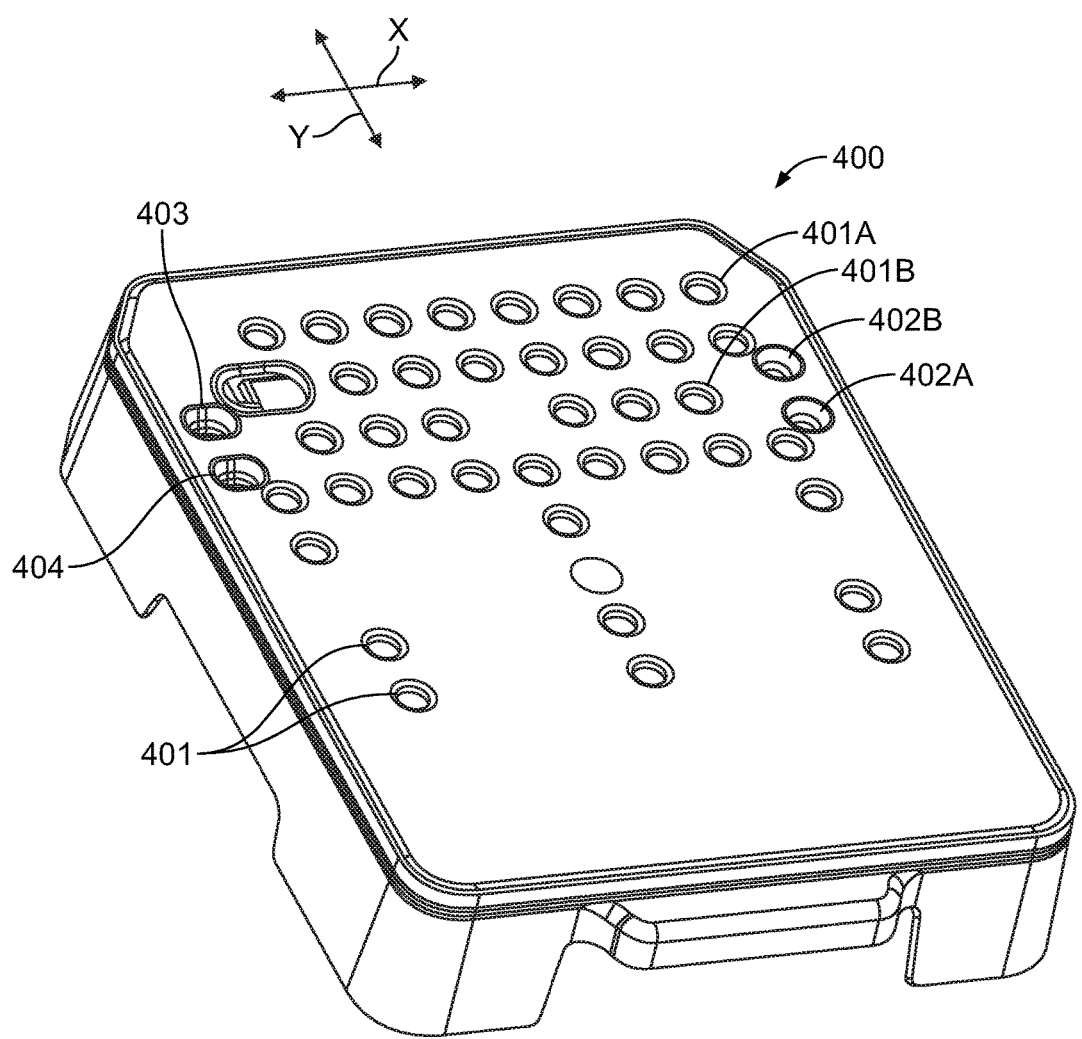
FIG. 3A shows a top perspective view of a reagent cartridge.

An exemplary reagent cartridge is shown in FIG. 3A. The reagent cartridge 400 shown in FIG. 3A can include wells 401 of varying depths along the z dimension compared to those of wells 402. More specifically, the reagent cartridge exemplified in FIG. 3A has wells designed to accommodate the length of a corresponding reagent sipper (not shown) such that each sipper reaches a desired depth in its corresponding reagent well when the sippers and the cartridge are in a fully engaged position. In the reagent cartridge exemplified in FIG. 3A, the wells are arranged in row or column along they dimension, where those wells 401 on the outside of the row or column extend downward further along the z dimension than those wells 402 on the inside of the row or column. Some or all of the wells can be of varying depths. Alternatively or additionally, some or all of the wells can be of the same depth. When the sippers and the cartridge are in a fully engaged position, the penetration depth of any sipper tip (i.e., the distance from the bottom surface of the well to the end of the sipper tip) can be equivalent to the penetration depth of any other sipper tip in any other given well in the reagent cartridge. The penetration depth of any sipper tip need not be the same as the penetration depth of any other given well in the reagent cartridge. Where at least some reagent wells have a different well depth, the well depth can be, for example, at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or at least 2.0 mm shorter than the other reagent sippers. Similarly, when the sippers and the cartridge are in a fully engaged position, the penetration depth of any sipper tip can be at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or at least 2.0 mm different than the penetration depth of any other sipper tip in the reagent cartridge.

As shown in the exemplary reagent cartridge 400 in FIG. 3A, the cartridge includes a plurality of reagent reservoirs

401A, 401B, 402A and 402B. The reagent reservoirs in FIG. 3A are arranged in x and y dimensions into rows. Also shown in FIG. 3A, the cartridge includes alignment slots 403 and 404 configured to engage with corresponding alignment pins of a manifold assembly (not shown). The cartridge may also include protective foil covering any number of the reagent wells or reservoirs, which can be pierced by piercing sippers when the cartridge is brought into contact with the piercing sippers.

The reagent cartridges presented herein can include any number of reagent reservoirs or wells. The reagent reservoirs or wells can be arranged in any format along the x and y dimensions to facilitate transport and storage of reagents in the cartridge. Alternatively or additionally, reagent reservoirs or wells can be arranged in any format along the x and y dimensions suitable for interaction with an array of sipper tubes extending downward along the z dimension from ports in the manifold. More specifically, the reagent reservoirs or wells can be arranged in any format suitable for simultaneously engaging a matrix of reagent sippers such that liquid reagent can be drawn from the reagent reservoir into the sippers.

Not all reagent wells need interact simultaneously with all sipper tubes of a manifold assembly. For example, the reagent cartridge can include a subset of one or more reagent reservoirs or wells that are configured to remain in a non-interacting state while other reservoirs or wells are engaged by an array of sipper tubes. As one example, a cartridge presented herein can comprises a plurality of wash reservoirs arranged in a configuration corresponding to the plurality of reagent reservoirs, whereby wash reservoirs are configured to simultaneously engage the reagent sippers when the reagent sippers are not engaged with the reagent reservoirs so that wash buffer can be drawn from the wash reservoirs into the sippers. An exemplary embodiment is presented in FIG. 3A, which shows a row of reagent wells 401A. The cartridge also includes a row of corresponding wells 401B which retains the same orientation in the x dimension with respect to each other, but which are offset in the y dimension from wells 401A. The offset wells 401B can include a wash buffer, for example, provided for rinsing sipper tubes and fluidic lines after using one cartridge and before using another cartridge.

Alternatively or additionally, other reservoirs that are empty, or which hold buffer, sample or other reagents can be present on the cartridge. The additional reservoirs can, but need not interact with a sipper tube. For example, a reservoir can be configured to be filled with waste or overflow reagent or buffer over the course of cartridge use. Such a reservoir may be accessed, for example via a port that does not interface with a sipper tube.

To facilitate correct alignment of cartridge reservoirs with corresponding sipper tubes, alignment slots can be positioned in the cartridge. For example, in particular embodiments where an array of sipper tubes is removed from one set of reservoirs and translocated to another set of reagent or wash reservoirs, alignment slots can be positioned in the cartridge to ensure correct alignment of the array of reagent sippers with one or both sets of reservoirs. As shown in FIG. 3A, the exemplary cartridge includes alignment slots 404 which retain the same orientation in the x dimension, but which are offset in the y dimension with respect to corresponding alignment slot 403. A cartridge of the embodiments presented herein can have any number of alignment slots which provide suitable alignment with the features of a fluidic assembly. For example, a cartridge can include 0, 1, 2, 3, 4, 5, 6, 7, 8, 9, 10 or more alignment slots configured to engage with corresponding alignment pins of the fluidic system so that reagent sippers of the fluidic system are positioned in alignment with the reagent and/or wash reservoirs.

Figure 19:
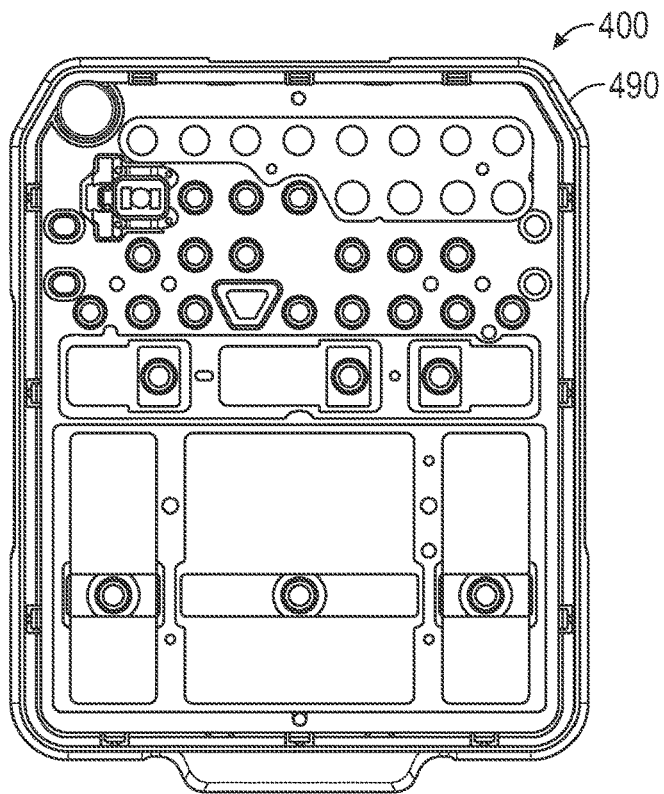
FIG. 19 is a plan view of a reagent cartridge with a cartridge cover or top removed in accordance with an embodiment.
Figure 20:
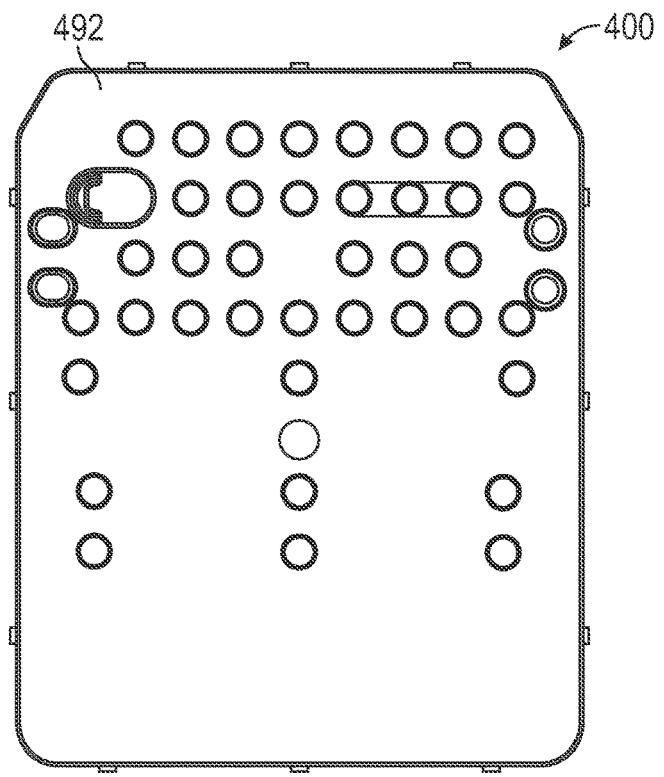
FIG. 20 is a plan view of the cartridge cover or top in accordance with an embodiment.

FIG. 19 illustrates positions of reservoirs relative to one another for the reagent cartridge 400. The reservoirs extend a depth into a housing or body 490 of the reagent cartridge 400. FIG. 20 is a plan view of a cover or top 492 that may be positioned onto the housing 490 reagent cartridge 400 to cover the reservoirs.

Figure 3B:
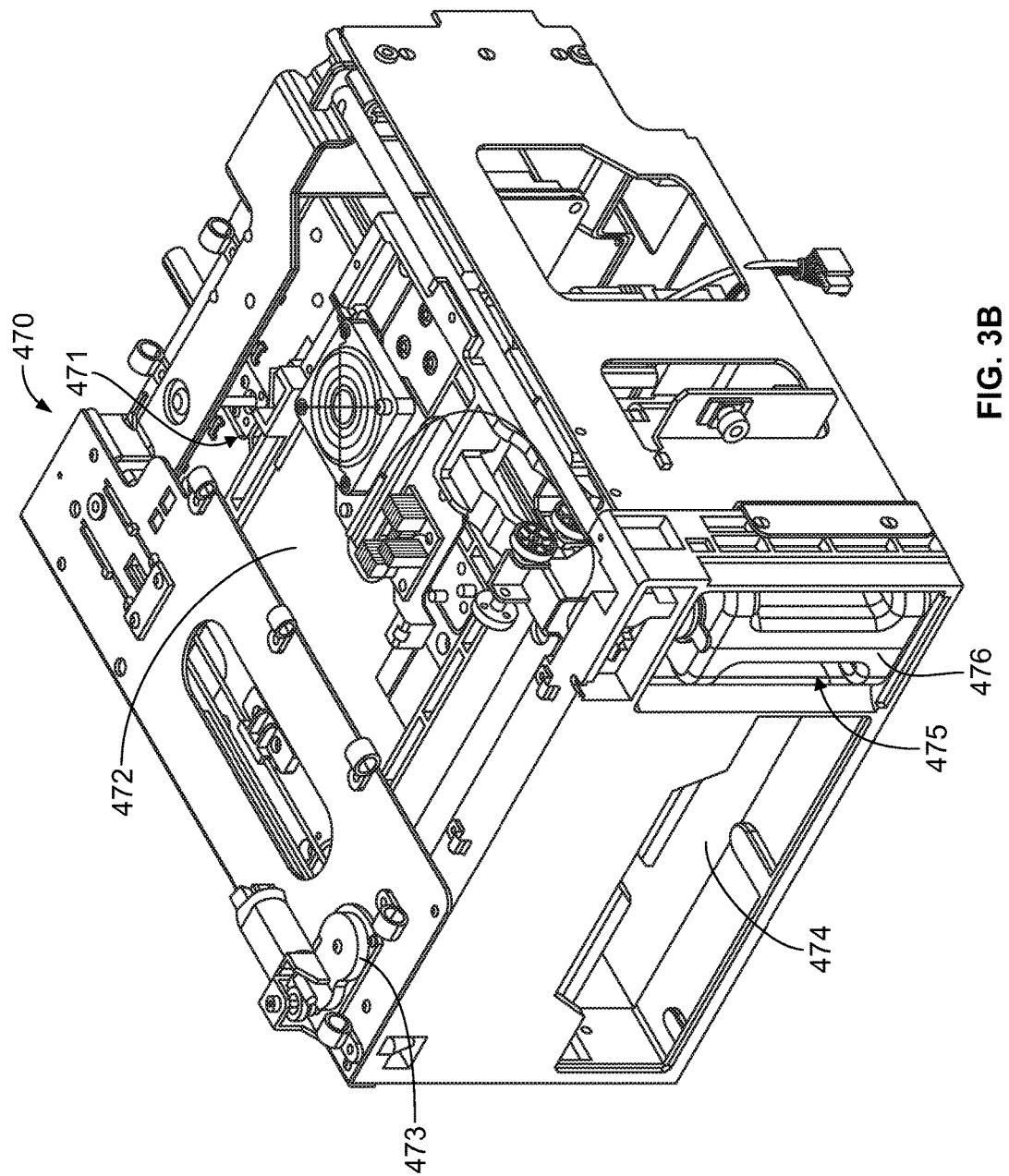
FIG. 3B shows a perspective view of a fluidics automation module.
Figure 8:
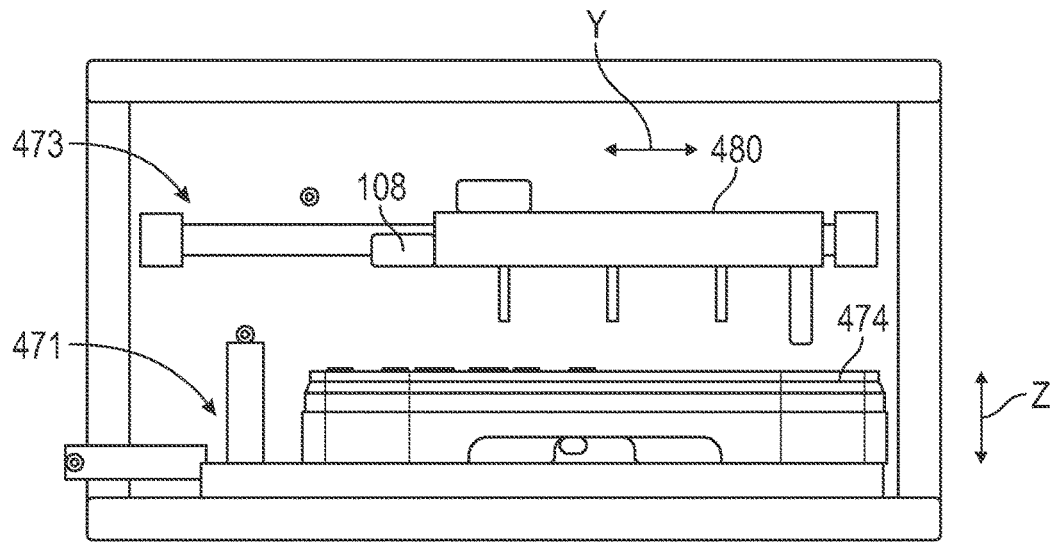
FIG. 8 is a schematic side view of elements of a fluidics automation module in accordance with an embodiment.

An exemplary fluidics automation module (FAM) is shown in FIG. 3B. FAM 470 can comprise lift assembly 471 for raising and lowering the reagent cartridge for piercing and bubble creation. Belt assembly 473 moves the reagent cartridge receptacle 474 during cartridge loading, and moves the reagent cartridge outside the device during unloading. Schematic side views of the lift assembly 471 and the belt assembly 473 are shown in FIG. 8. A waste reservoir receptacle 475 is also present on the front face of the FAM 470 and is configured to accept waste reservoir 476. FAM 470 further comprises a manifold assembly 472, which is set forth in greater detail in FIG. 2B. In some embodiments, the belt assembly 473 (or another motorized assembly) may directly or indirectly move the manifold body 108 relative to the reagent cartridge 474. The manifold assembly 472 may include a manifold carriage 480 (shown in FIG. 8). The manifold carriage 480 may be coupled to the manifold body 108 such that the manifold body and the manifold carriage 480 have essentially fixed positions relative to one another during operation. For example, the manifold carriage 480 holds the manifold body 108. The manifold carriage 480 may be movable by the belt assembly 473 (or other motorized assembly) along the Y-axis.

Provided herein is a detection apparatus, having (a) a carriage including a one or more microfluorometers, wherein each of the microfluorometers includes an objective configured for wide-field image detection, wherein the one or more microfluorometers is positioned to acquire one or more wide-field images in a common plane, and wherein each of the wide-field images is from a different area of the common plane; (b) a translation stage configured to move the carriage in at least one direction parallel to the common plane; and (c) a sample stage configured to hold a substrate in the common plane.

A detection apparatus (or an individual microfluorometer) of the present disclosure can be used to obtain one or more images at a resolution that is sufficient to distinguish features on a micron scale. For example, a microfluorometer that is used in a detection apparatus can have a resolution that is sufficient to distinguish features that are separated by at most 500 µm, 100 µm, 50 µm, 10 µm, 5 µm, 4 µm, 3 µm, 2 µm or 1 µm. Lower resolution is also possible, for example, a resolution that distinguishes features that are separated by more than 500 µm.

A detection apparatus (or an individual microfluorometer) of the present disclosure is well suited for high-resolution detection of surfaces. Accordingly, arrays having features with average spacing in the micron range are especially useful substrates. In particular embodiments, a detection apparatus or microfluorometer can be used to obtain one or more images of an array having features with center-to-center spacing for nearest neighbors that is on average at or below 500 µm, 100 µm, 50 µm, 10 µm, 5 µm, 4 µm, 3 µm, 2 µm or 1 µm. In many embodiments the features of an array are non-contiguous being separated, for example, by less than 100 µm, 50 µm, 10 µm, 5 µm, 1 µm, or 0.5 µm.

However, the features need not be separated. Instead some or all of the features of an array can be contiguous with each other.

Any of a variety of arrays (also referred to as "microarrays") known in the art can be used. A typical array contains features, each having an individual probe or a population of probes. In the latter case, the population of probes at each site is typically homogenous having a single species of probe. For example, in the case of a nucleic acid array, each feature can have multiple nucleic acid species each having a common sequence. However, in some embodiments the populations at each feature of an array can be heterogeneous. Similarly, protein arrays can have features with a single protein or a population of proteins typically, but not always, having the same amino acid sequence. The probes can be attached to the surface of an array for example, via covalent linkage of the probes to the surface or via non-covalent interaction(s) of the probes with the surface. In some embodiments, probes, such as nucleic acid molecules, can be attached to a surface via a gel layer as described, for example, in US 2011/0059865 A1, which is incorporated herein by reference.

Exemplary arrays include, without limitation, a BeadChip Array available from Illumina , Inc. (San Diego, Calif.) or others such as those where probes are attached to beads that are present on a surface (e.g. beads in wells on a surface) such as those described in U.S. Pat. Nos. 6,266,459; 6,355, 431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in an apparatus or system according to some embodiments of the invention. An exemplary spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, or US 2008/0108082, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US 2005/0130173 or US 2005/0064460, each of which is incorporated herein by reference in its entirety. Although the above arrays have been described in the context of sequencing applications, it will be understood that the arrays can be used in other embodiments including, for example, those that do not include a sequencing technique.

Whether configured for detection of an array or other sample, one or more microfluorometers that are present in a detection apparatus can be configured for wide-field detection. The field diameter for an individual microfluorometer can be, for example, at least 0.5 mm, 1 mm, 2 mm, 3 mm, 4 mm, 5 mm or larger. By choice of appropriate optical components the field diameter can be limited to a maximum area as well and, as such the field diameter can be, for example, no larger than 5 mm, 4 mm, 3 mm, 2 mm or 1 mm. Accordingly, in some embodiments an image obtained by an individual microfluorometer can have an area that is in a range of 0.25 mm$^2$ to 25 mm$^2$.

In addition to being configured for wide-field detection, a microfluorometer can be configured to have a numerical aperture (NA) that is greater than 0.2. For example, the NA of an objective used in a microfluorometer of the present disclosure can be at least 0.2, 0.3, 0.4, or 0.5. Alternatively or additionally, it may be desirable to restrict the NA of the objective to be no greater than 0.8, 0.7, 0.6 or 0.5. The methods and apparatus set forth herein are particularly useful when detection occurs through an objective having a NA between 0.2 and 0.5.

In array detection embodiments, a detection apparatus (or individual microfluorometer) can be configured to obtain a digital image of the array. Typically, each pixel of the digital detection apparatus (or individual microfluorometer) will collect signal from no more than a single feature in any given image acquisition. This configuration minimizes unwanted 'cross talk' between features in the image. The number of pixels that detect signal from each feature can be adjusted based on the size and shape of the features imaged and based on the configuration of the digital detection apparatus (or individual microfluorometer). For example, each feature can be detected in a given image by no more than about 16 pixels, 9 pixels, 4 pixels, or 1 pixel. In particular embodiments, each image can utilize on average 6.5 pixels per feature, 4.7 pixels per feature or 1 pixel per feature. The number of pixels used per feature can be reduced, for example, by reducing variability in the position of features in the pattern of the array and tightening the tolerance for alignment of the detection apparatus to the array. Taking as an example a digital detector that is configured to use fewer than 4 pixels per feature, image quality can be improved by using an array of ordered nucleic acid features in place of an array of randomly distributed nucleic acid clusters.

It will be understood that a detection apparatus having one or more microfluorometers can detect an area of a common plane that is roughly equivalent to the number of microfluorometers multiplied by the wide-field area detected by each microfluorometer. The areas need not be contiguous. For example, 2 or more microfluorometers can be positioned to detect discrete regions of a common plane that are separated by an undetected area. However, if desired, multiple microfluorometers can be positioned to detect areas that are contiguous, but not overlapping. In alternative embodiments a detection apparatus having one or more microfluorometers can detect an area of a common plane that is substantially less than the number of microfluorometers multiplied by the wide-field area detected by each microfluorometer. This can result, for example, when multiple microfluorometers are positioned to detect areas that have at least a partial overlap. As set forth in further detail elsewhere herein, multiple images need not be acquired in a format that is used for or that even supports reconstruction of a complete image of an array or other common plane that has been detected.

The detection apparatus can make use of any of the detection apparatus configurations and sequencing methods set forth in U.S. patent application Ser. No. 13/766,413 filed on Feb. 13, 2013 and entitled "INTEGRATED OPTOELECTRONIC READ HEAD AND FLUIDIC CARTRIDGE USEFUL FOR NUCLEIC ACID SEQUENCING," the content of which is incorporated by reference in its entirety.

The exemplary detection apparatus presented herein is shown having a single microfluorometer. In other embodiments, the detection apparatus can have two or more microfluorometer, in any one of a variety of configurations. It will be appreciated that a single microfluorometer can be advantageous from a variety of standpoints. First, the single microfluorometer provides advantages from the standpoint of production and maintenance costs, especially when other configurations require calibration of each individual microfluorometer. In the single microfluorometer configuration presented herein, the optical readhead can be presented in an intact unit that can be incorporated into the detection apparatus in a modular approach, simplifying manufacturing and reducing costs further. These costs savings can be passed along to the end user, allowing users access to a large number of nucleic acid array detection applications. Another advantage of the single microfluorometer configuration presented herein comes from the relative simplicity of the interactions with the fluidic components of the system. For example, a flow cell used in the system can be configured with a single flow channel, thus reducing the requirements for multiple valves and pumps found in prior systems. Whereas flow cells having 2 or more flow channels may require switching fluid flow between different flow channels, a single flow channel can have a dedicated supply line in fluid communication with a single valve. Additionally, fluidic manifold bodies can be used having a single layer of channels, again simplifying the design and manufacture of the fluidic system and reducing costs of fabrication and maintenance of the system.

Figure 4A:
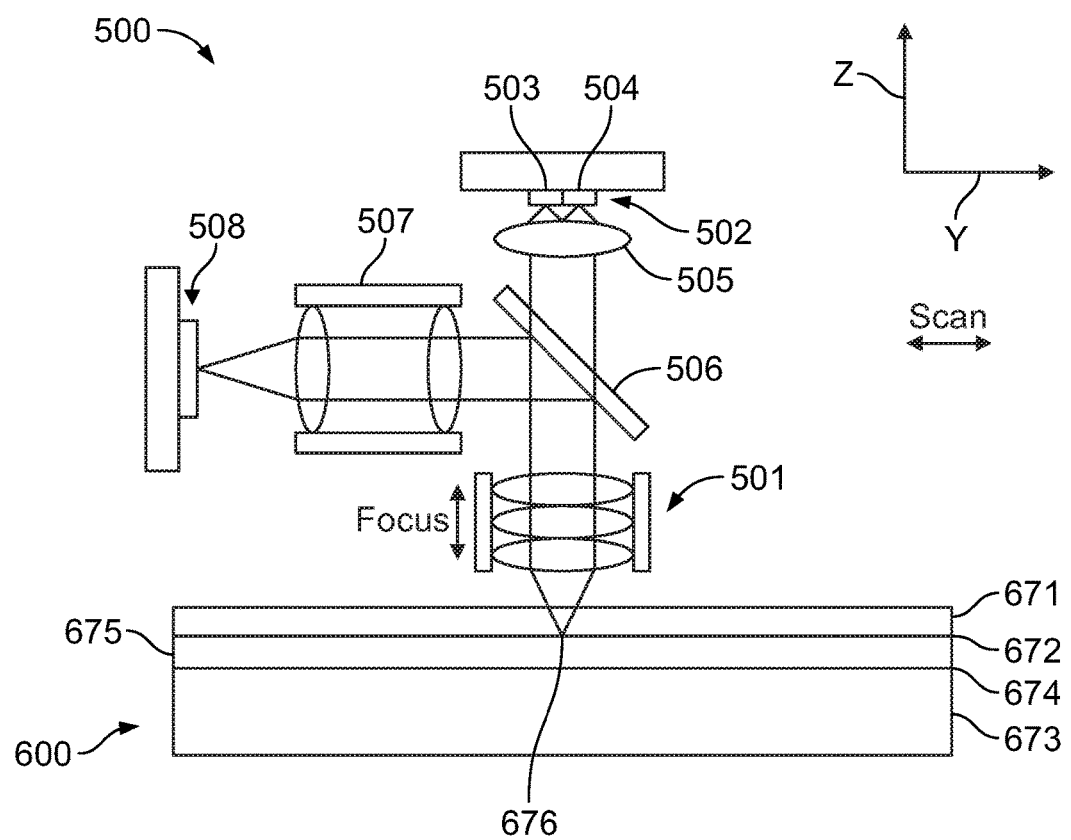
FIG. 4A shows an optical layout for an individual microfluorometer having orthogonal excitation and emission beam paths.

An exemplary optical layout for a microfluorometer 500 is shown in FIG. 4A. The microfluorometer 500 is directed to a flow cell 600 having an upper layer 671 and a lower layer 673 that are separated by a fluid filled channel 675. In the configuration shown, the upper layer 671 is optically transparent and the microfluorometer 500 is focused to an area 676 on the inner surface 672 of the upper layer 671. In an alternative configuration the microfluorometer 500 can be focused on the inner surface 674 of the lower layer 673. One or both of the surfaces can include array features that are to be detected by the microfluorometer 500.

The microfluorometer 500 includes an objective 501 that is configured to direct excitation radiation from a radiation source 502 to the flow cell 600 and to direct emission from the flow cell 600 to a detector 508. In the exemplary layout, excitation radiation from the radiation source 502 passes through a lens 505 then though a beam splitter 506 and then through the objective on its way to the flow cell 600. In the embodiment shown the radiation source includes two light emitting diodes (LEDs) 503 and 504, which produce radiation at different wavelengths from each other. The emission radiation from the flow cell 600 is captured by the objective 501 and is reflected by the beam splitter through conditioning optics 507 and to the detector 508 (e.g. a CMOS sensor). The beam splitter 506 functions to direct the emission radiation in a direction that is orthogonal to the path of the excitation radiation. The position of the objective can be moved in the z dimension to alter focus of the microfluorometer. The microfluorometer 500 can be moved back and forth in the y direction to capture images of several areas of the inner surface 672 of the upper layer 671 of the flow cell 600.

Figure 4B:
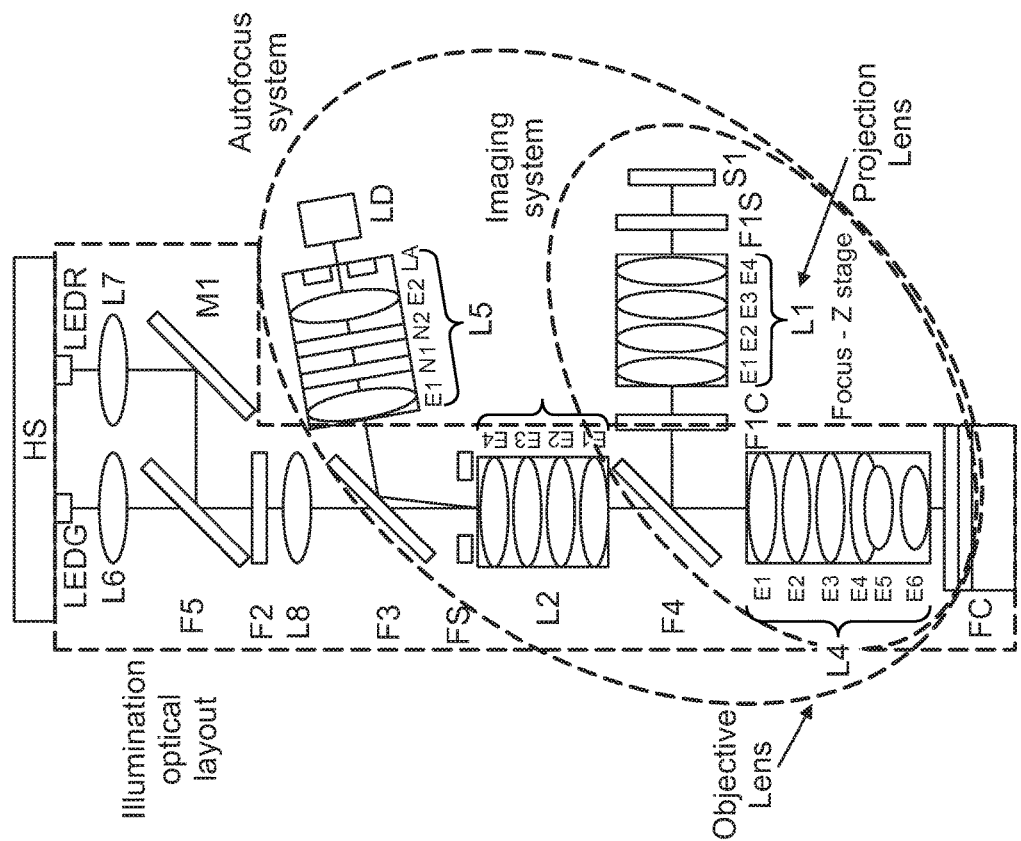
FIG. 4B shows an optical layout for a microfluorometer.

FIG. 4B shows an exploded view of an exemplary microfluorometer for purposes of demonstrating functional arrangement for various optical components. Two excitation sources are shown, including a green LED (LEDG) and a red LED (LEDR). Excitation light from each passes through a green LED collector lens (L6) and red LED collector lens (L7), respectively. The green excitation radiation passes from the green LED collector lens (L6) to the combiner dichroic (F5) which reflects the green excitation radiation through an excitation filter (F2), then through a an LED field lens (L8) and laser diode beam splitter (F3), then through an excitation field stop (FS), then through an excitation projection lens group L2 to an excitation/emission dichroic (F4) which reflects the green excitation radiation through an objective lens group (L4) to the surface of a flow cell (FC). An LED fold mirror (M1) reflects the red excitation radiation to a combiner dichroic (F5) after which the red excitation radiation follows the same path as the green excitation radiation to the surface of the flow cell (FC). As shown in the figure, focusing is actuated by moving the translating objective lens group (L4) up and down (i.e. along the z dimension). Emission from the flow cell (FC) surface passes back through the translating objective lens group (L4), to the excitation/emission dichroic (F4) which passes the emission radiation to the emission projection lens group (L1) through to the emission filter and then to the CMOS image sensor (S1). A laser diode (LD) is also directed via a laser diode coupling lens group (L5) to the laser diode beam splitter (F3) which reflects the laser diode radiation through the excitation field stop (FS), the excitation projection lens group (L2), the excitation/emission dichroic (F4), objective lens group (L4) to the flow cell (FC). An LED heat sink (HS) is disposed above the green LED (LEDG) and red LED (LEDR).

Figure 4C:
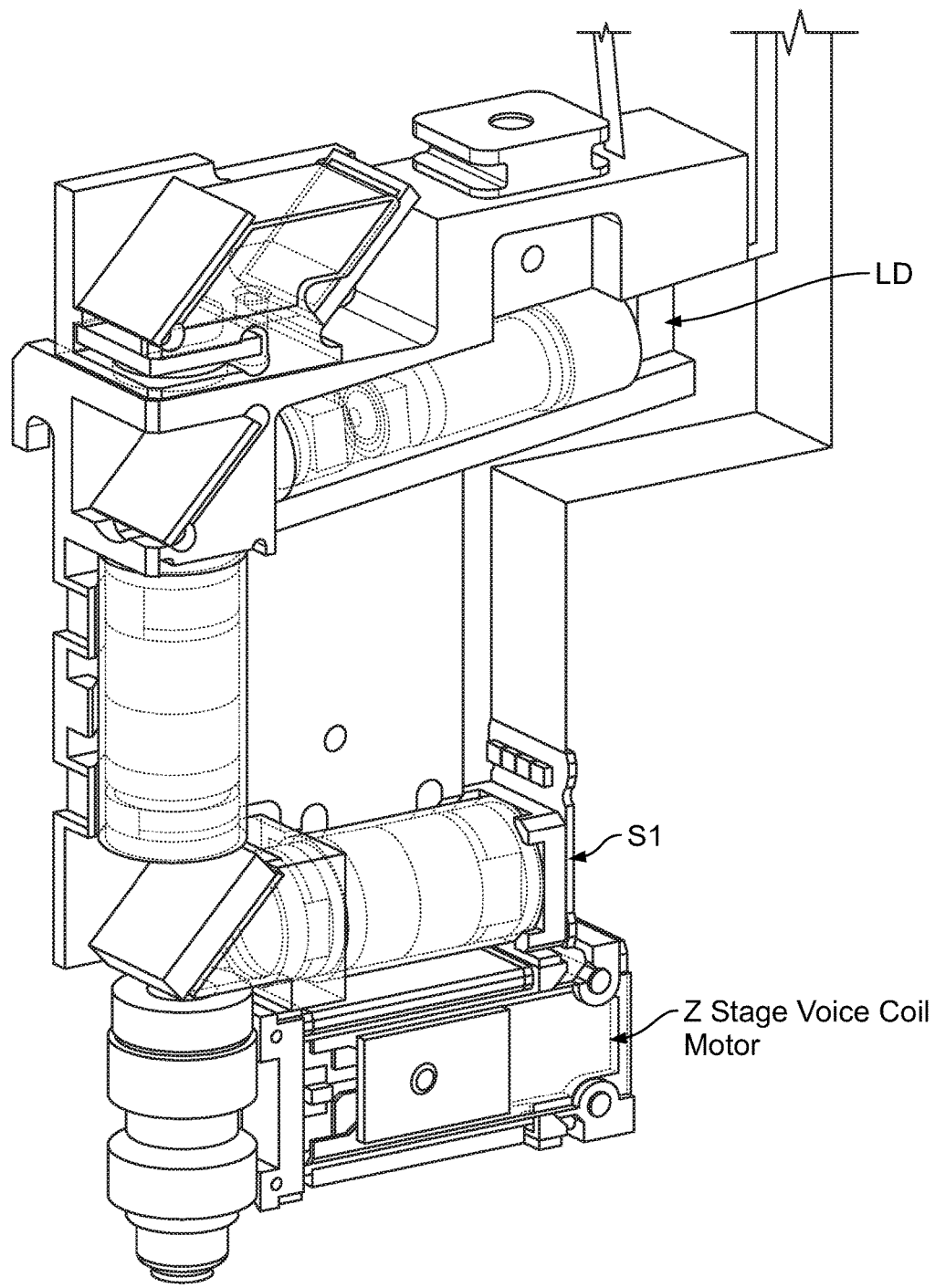
FIG. 4C shows a perspective view of an exemplary single microfluorometer.

FIG. 4C shows an exemplary embodiment of a single camera module, including laser diode (LD) for autofocus system, CMOS image sensor (S1) and Z stage voice coil motor for adjusting objective lens (L4). LEDG and LEDR are not shown in this view.

As demonstrated by the exemplary embodiments of FIGS. 4A, 4B and 4C, each of the microfluorometers can include a beam splitter and a detector, wherein the beam splitter is positioned to direct excitation radiation from an excitation radiation source to the objective and to direct emission radiation from the objective to the detector. As shown in the figures, each microfluorometer can optionally include an excitation radiation source such as an LED. In this case, each microfluorometer can include a dedicated radiation source, such that the read head includes several radiation sources each separated into individual microfluorometers. In some embodiments, two or more microfluorometers can receive excitation radiation from a common radiation source. As such the two or more microfluorometers can share a radiation source. In an exemplary configuration, a single radiation source can direct radiation to a beam splitter that is positioned to separate the excitation radiation into two or more beams and directs the beams to two or more respective microfluorometers. Additionally or alternatively, excitation radiation can be directed from a radiation source to one, two or more microfluorometers via one or more optical fibers.

It will be understood that the particular components shown in the figures are exemplary and can be replaced with components of similar function. For example, any of a variety of radiation sources can be used instead of an LED. Particularly useful radiation sources are arc lamps, lasers, semiconductor light sources (SLSs), or laser diodes. LEDs can be purchased, for example, from Luminus (Billerica, Mass). Similarly, a variety of detectors are useful including, but not limited to a charge-coupled device (CCD) sensor; photomultiplier tubes (PMT's); or complementary metal-oxide-semiconductor (CMOS) sensor. A particularly useful detector is a 5-megapixel CMOS sensor (MT9P031) available from Aptina Imaging (San Jose, Calif.).

FIGS. 4A, 4B and 4C provide exemplary embodiments of a microfluorometer that includes two excitation sources. This configuration is useful for detecting at least two fluorophores that are excited at different wavelengths, respectively. If desired, a microfluorometer can be configured to include more than two excitation sources. For example, a microfluorometer can include at least 2, 3, 4 or more different excitation sources (i.e. sources producing different wavelengths from each other). Alternatively or additionally, beam splitters and optical filters can be used to expand the range of excitation wavelengths available from an individual radiation source. Similar use of multiple radiation sources and/or optical filtering of split excitation beams can be used for embodiments where several microfluorometers share excitation from one or more radiation sources. As set forth in further detail elsewhere herein, the availability of multiple excitation wavelengths is particularly useful for sequencing applications that utilize several different fluorophore labels.

Figure 5A:
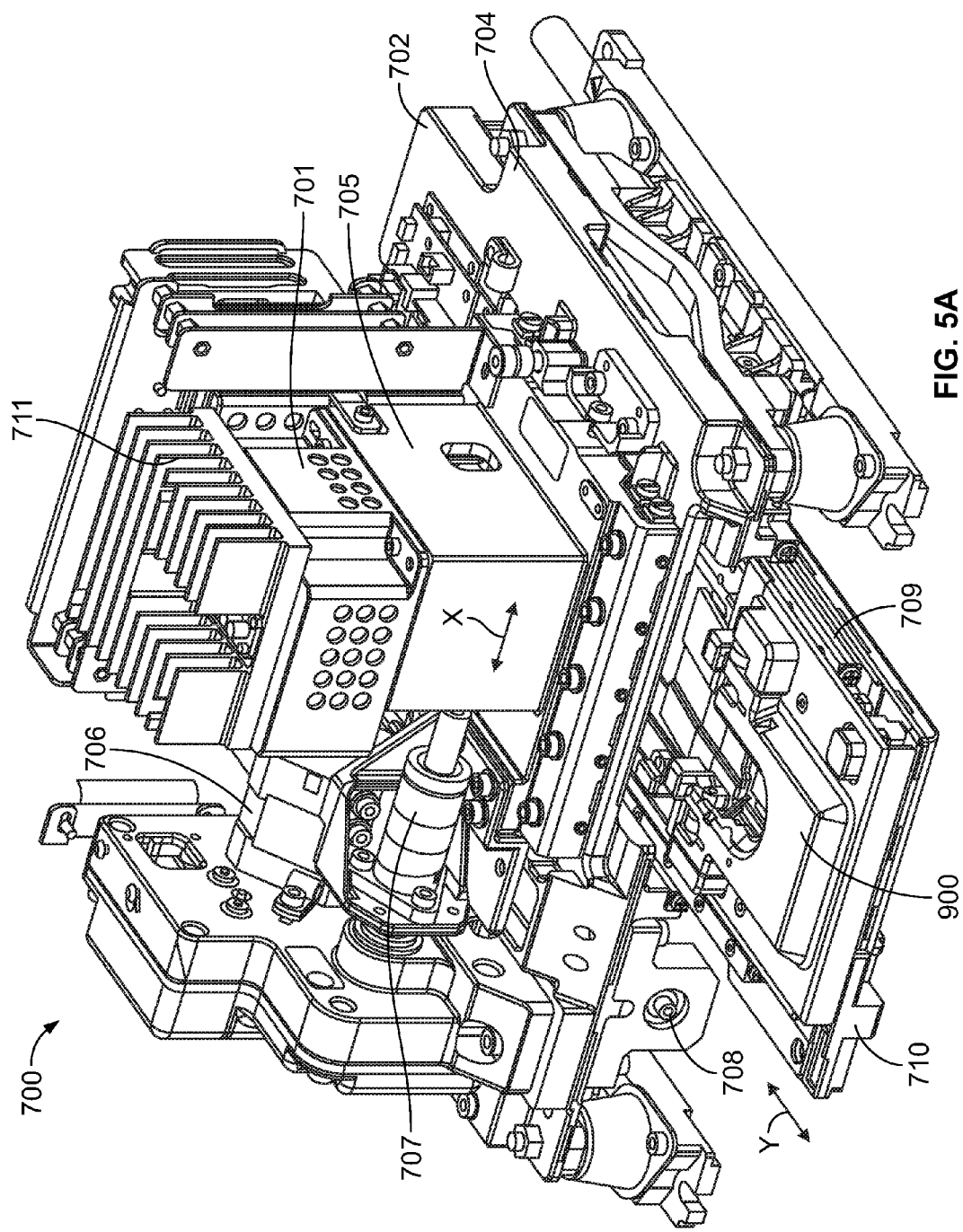
FIG. 5A shows a front perspective view of an imaging module having a single microfluorometer.

The microfluorometer of the exemplary embodiment is a component of an imaging module. FIG. 5A sets forth a front view of one exemplary embodiment. Shown is imaging module 700, made up of camera assembly 701, XY stage 702, and flow cell latch clamp module 900, mounted to fixed base 704. Camera assembly comprises heat sink 711 above camera housing 705, which in turn is mounted to fixed base 704 and provides an enclosure for the lower half of the microfluorometer set forth in FIGS. 4A, 4B and 4C. Two motors provide movement of X-stage and Y-stage, individually. X-motor 706 drives X lead screw 707 which moves camera assembly 701 along X-axis as indicated. Y-motor (712, not shown) drives movement of Y lead screw 708 which moves flow cell latch clamp module 900 along Y-axis on guide rail 709 as indicated. The flow cell latch clamp module 900 can also comprise an RFID module 710 for detecting RFID encoded flow cells.

Figure 5B:
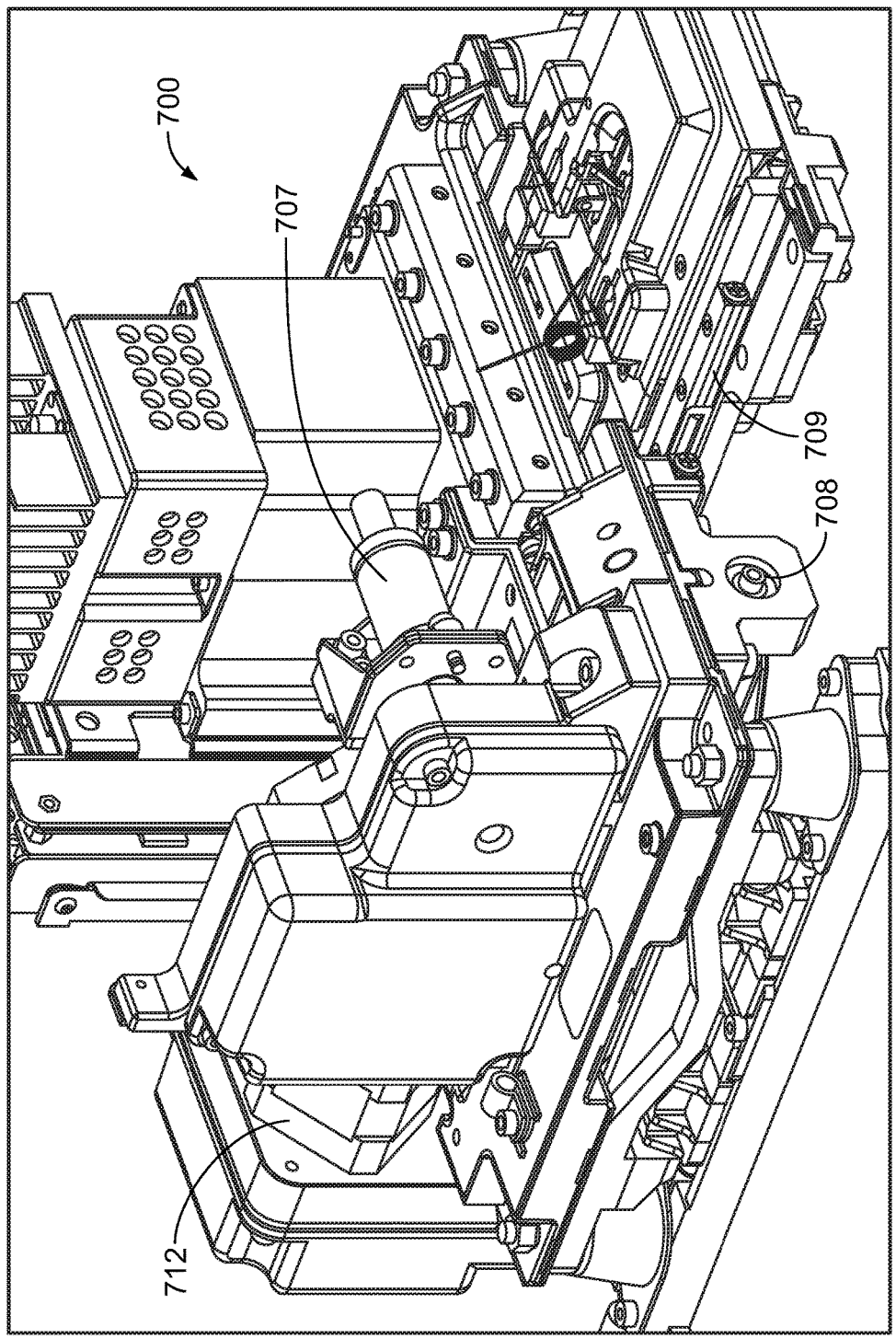
FIG. 5B shows a side perspective view of an imaging module having a single microfluorometer.

FIG. 5B shows a side view of the imaging module 700. Shown is Y-motor 712, Y lead screw 708, guide rail 709 and X-lead screw 707.

In accordance with one embodiment, a fluidic device for analyzing samples is provided. The fluidic device includes a flow cell having inlet and outlet ports and a flow channel extending therebetween. The flow cell is configured to hold a sample-of-interest. The fluidic device also includes a housing having a reception space that is configured to receive the flow cell. The reception space is sized and shaped to permit the flow cell to float relative to the housing. The fluidic device also includes a gasket that is coupled to the housing. The gasket has inlet and outlet passages and comprises a compressible material. The gasket is positioned relative to the reception space so that the inlet and outlet ports of the flow cell are approximately aligned with the inlet and outlet passages of the gasket, respectively.

In another embodiment, a removable cartridge configured to hold and facilitate positioning a flow cell for imaging is provided. The cartridge includes a removable housing that has a reception space configured to hold the flow cell substantially within an object plane. The housing includes a pair of housing sides that face in opposite directions. The reception space extends along at least one of the housing sides so that the flow cell is exposed to an exterior of the housing through at least one of the housing sides. The cartridge also includes a cover member that is coupled to the housing and includes a gasket. The gasket has inlet and outlet passages and comprises a compressible material. The gasket is configured to be mounted over an exposed portion of the flow cell when the flow cell is held by the housing.

Exemplary fluidic devices, including flow cells suitable for use with the devices described herein are set forth greater detail in U.S. patent application Ser. No. 13/766,413 filed on Feb. 13, 2013 and entitled "INTEGRATED OPTOELECTRONIC READ HEAD AND FLUIDIC CARTRIDGE USEFUL FOR NUCLEIC ACID SEQUENCING," the content of which is incorporated by reference in its entirety.

Figure 6:
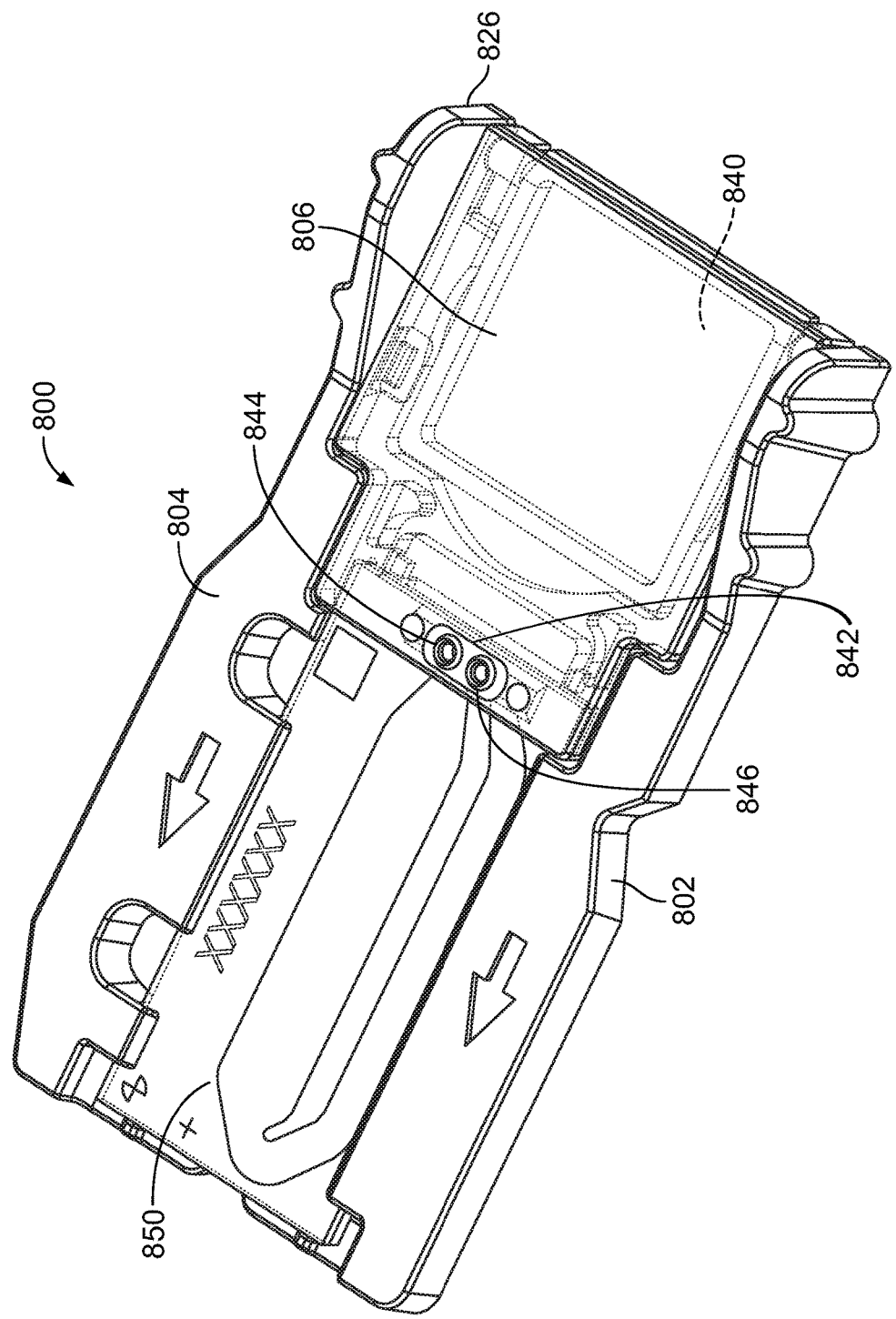
FIG. 6 shows a flow cell.

FIG. 6 illustrates a fluidic device 800 formed in accordance with one embodiment. As shown in FIG. 6, the fluidic device 800 includes a cartridge (or flow cell carrier) 802 and the flow cell 850. The cartridge 802 is configured to hold the flow cell 850 and facilitate orienting the flow cell 850 for an imaging session.

In some embodiments, the fluidic device 800 and the cartridge 802 may be removable such that the cartridge 802 may be removed from an imaging system (not shown) by an individual or machine without damage to the fluidic device 800 or cartridge 802. For example, the cartridge 802 may be configured to be repeatedly inserted and removed into the imaging system without damaging the cartridge 802 or rendering the cartridge 802 unsuitable for its intended purpose. In some embodiments, the fluidic device 800 and the cartridge 802 may be sized and shaped to be handheld by an individual. Furthermore, the fluidic device 800 and the cartridge 802 may be sized and shaped to be carried by an automated system.

As shown in FIG. 6, the cartridge 802 may include a housing or carrier frame 804 and a cover member 806 that is coupled to the housing 804. Also shown in FIG. 6, the fluidic device 800 may have a device window that passes entirely through the cartridge 802 along the Z-axis. With respect to FIG. 6, the cover member 806 may include a cover body 840 and a gasket 842 that are coupled to each other. The gasket 842 includes inlet and outlet passages 846 and 844 that are located proximate to one another. In the illustrated embodiment, the cover body 840 and the gasket 842 are co-molded into a unitary structure. When formed, the cover body 840 and the gasket 842 may have different compressible properties. For example, in particular embodiments, the gasket 842 may comprise a material that is more compressible than material of the cover body 840. However, in alternative embodiments, the cover body 840 and the gasket 842 may be separate parts that are coupled together (e.g., mechanically or using an adhesive). In other embodiments, the cover body 840 and the gasket 842 may be different portions or regions of a single continuous structure.

The cover member 806 may be movably coupled to the housing 804. For example, the cover member 806 may be rotatably coupled to the base member 826 of the housing 804. The housing 804 may define a cartridge cavity that is accessible when the cover member 806 is in the disengaged position. In some embodiments, an identification transmitter may be positioned within the cartridge cavity. The identification transmitter is configured to communicate information about the flow cell 850 to a reader. For example, the identification transmitter may be an RFID tag. The information provided by the identification transmitter may, for example, identify the sample in the flow cell 850, a lot number of the flow cell or sample, a date of manufacture, and/or the assay protocol to be performed when the flow cell 850 is inserted into the imaging system. The identification transmitter may communicate other information as well.

Figure 7A:
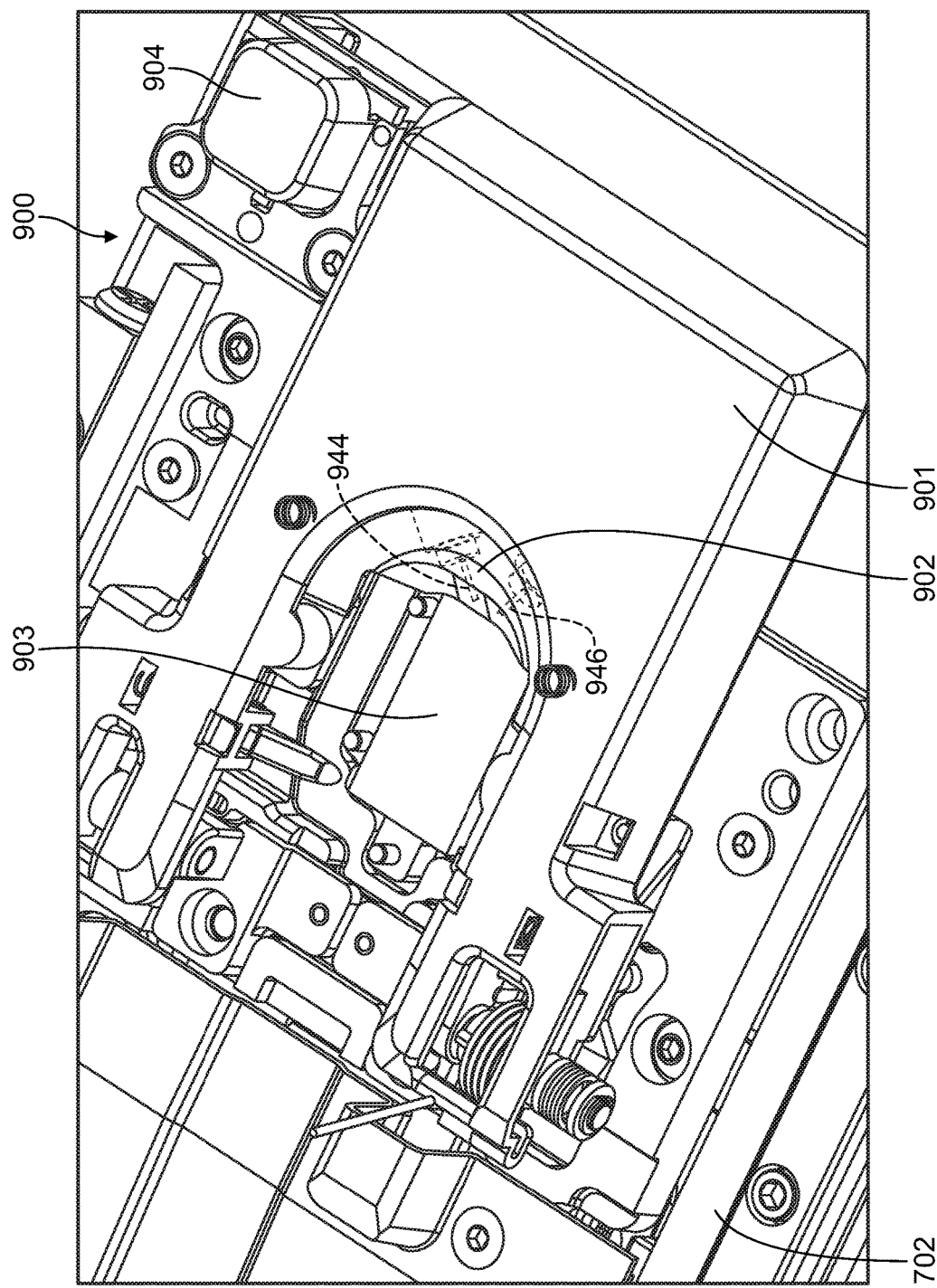
FIG. 7A shows a perspective view of a flow cell latch clamp module.

Shown in FIG. 7A is a flow cell latch clamp module (FCLM) 900 (hereinafter referred to as latch clamp module), is mounted directly on the Y-plate of the XY stage 702. Flow cell latch clamp cover 901 holds the flow cell 800 and aligns it to the camera in the microfluorometer. Within clamp cover 901 is a cover manifold 902 with inlet and outlet ports 944, 946 configured to mate with inlet passage 846 and outlet passage 844 positions in the gasket of flow cell housing. A heat block 903 is mounted to Y-plate and provides heating to the flow cell to enable chemistry. Latch button 904 can be depressed to open clamp cover 901.

Figure 7B:
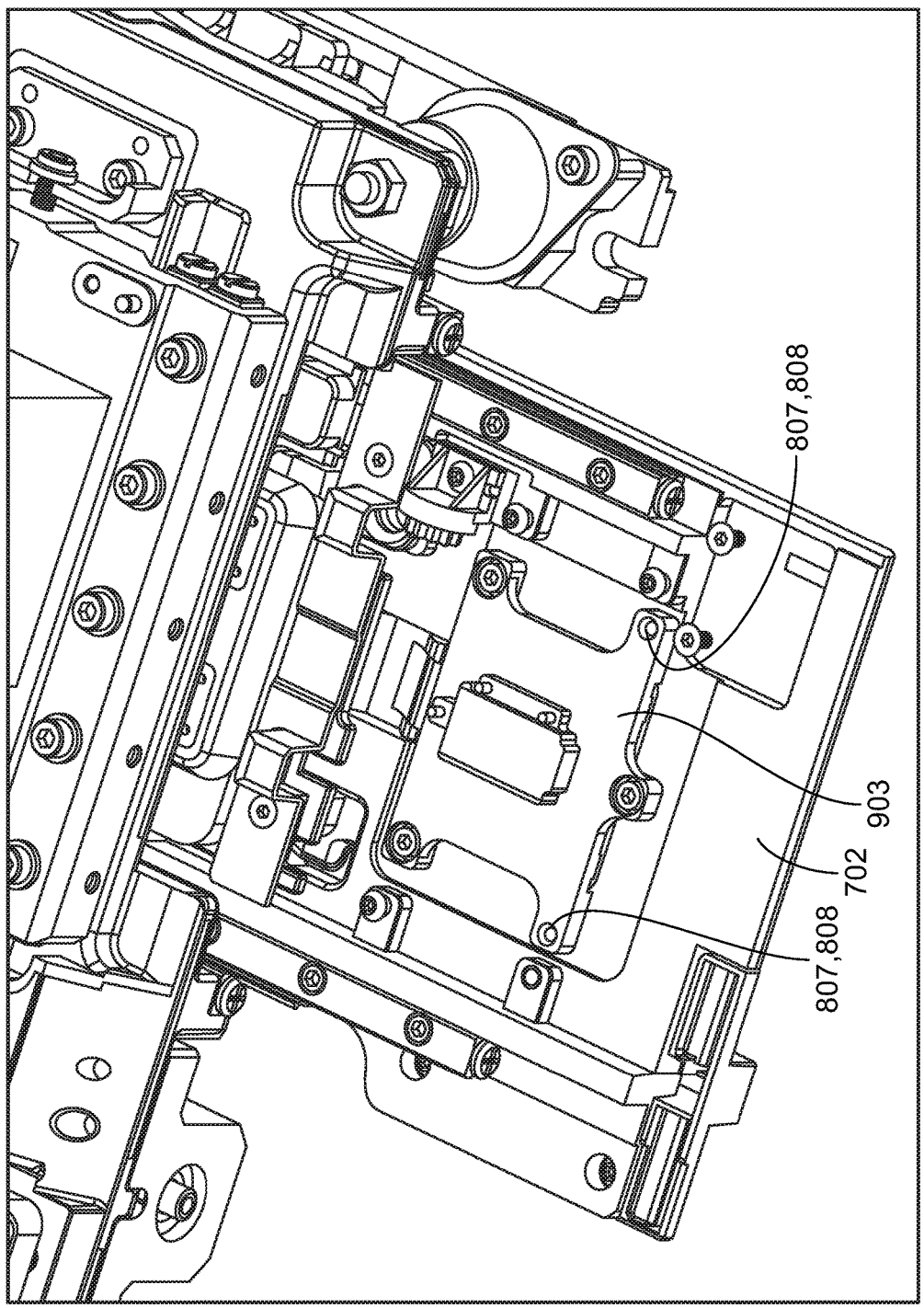
FIG. 7B shows flow cell latch clamp module without flow cell or cover.
Figure 7C:
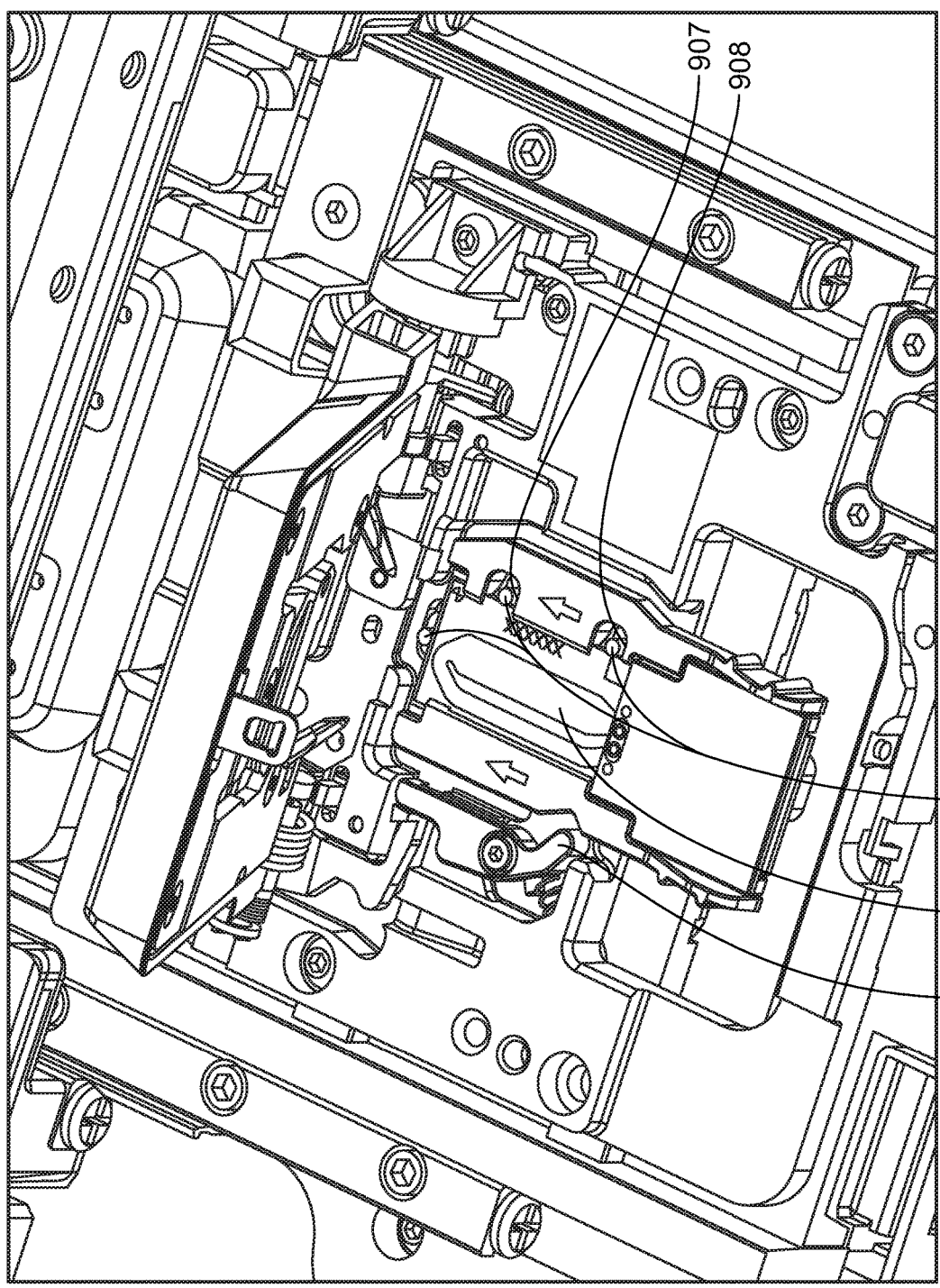
FIG. 7C shows flow cell mounted in latch clamp module with cover in unlatched position.

FIG. 7B shows a cutaway view of latch clamp module 900, showing heat block 903 mounted directly to imaging module Y-plate 702. FIG. 7C shows latch clamp module 900 with flow cell 850 mounted in position. Flow cell datum edges 807 and 808 are biased against another set of dowel pins 907 and 908 mounted to heater block. Spring-loaded lever 909 biases the flow cell 850 against the heater block dowel pins 907 and 908. As shown, flow cell 850 is registered in X and Y positions against reference pins and in Z position against heater block surface. The flow cell clamp module 900 provides sealing for fluidics, supporting negative and positive pressure in the fluidic connection between the FAM and the flow cell gasket.

The embodiments shown in FIGS. 7A, 7B and 7C are exemplary. Further exemplary embodiments of the methods and apparatus of the present disclosure that can be used alternatively or additionally to the example of FIGS. 7A, 7B and 7C are set forth in further detail in U.S. patent application Ser. No. 13/766,413 filed on Feb. 13, 2013 and entitled "INTEGRATED OPTOELECTRONIC READ HEAD AND FLUIDIC CARTRIDGE USEFUL FOR NUCLEIC ACID SEQUENCING," the content of which is incorporated by reference in its entirety.

Figure 10:
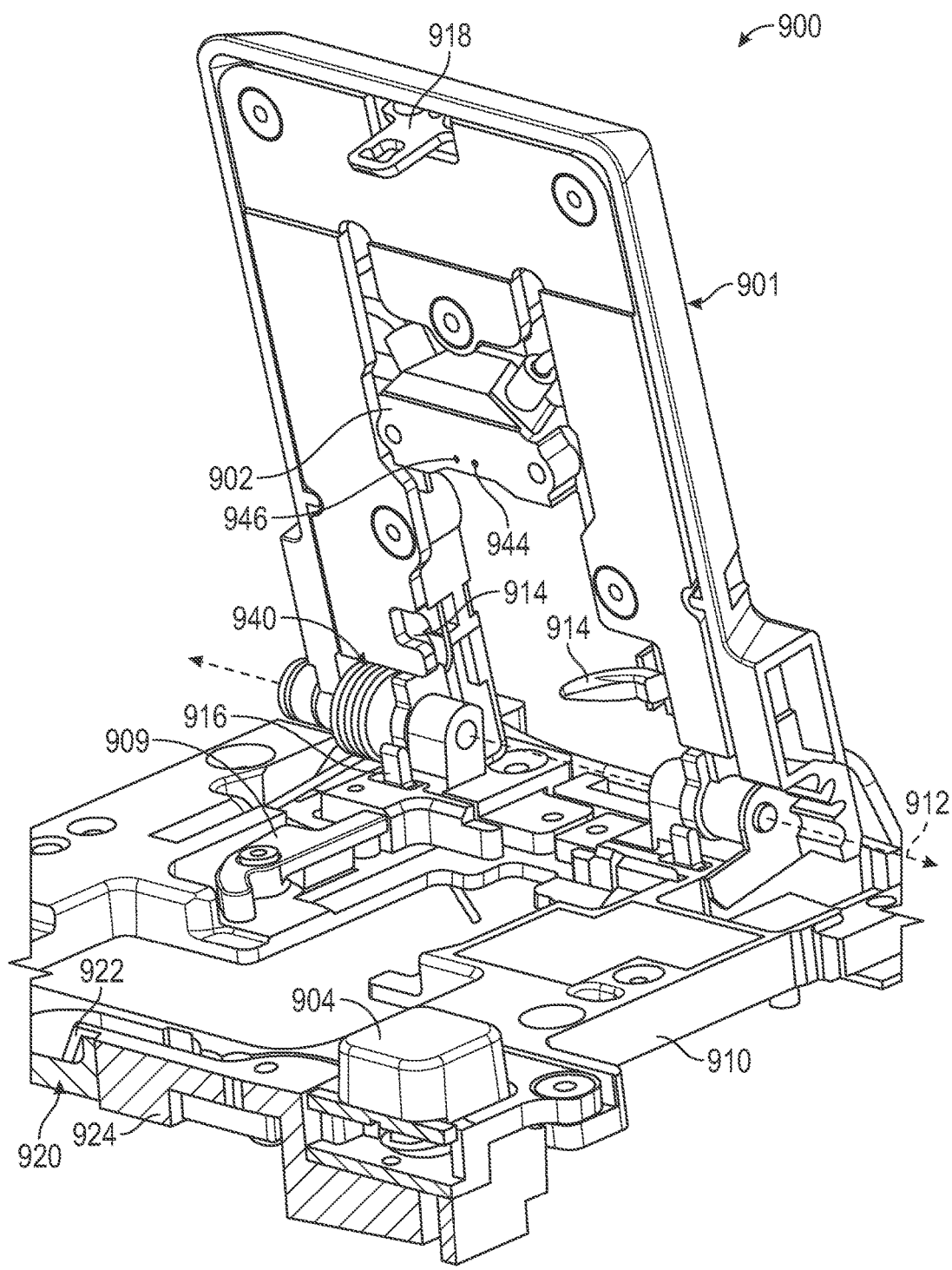
FIG. 10 is an enlarged perspective view of a portion of a flow cell latch clamp module in accordance with an embodiment.

FIG. 10 is a perspective of a portion of the FCLM 900. The clamp cover 901, the cover manifold 902, the latch button 904, and the spring-loaded lever 909 are shown. The FCLM 900 also includes a clamp base 910. The clamp cover 901 is rotatably coupled to the clamp base 910 and is configured to rotate about an axis 912. Also shown, the FCLM 900 includes legs 914 and a biasing member 916. Each of the legs 914 is configured to engage the fluidic device. Optionally, the legs 914 may engage the flow cell directly. Inlet and outlet ports 944, 946 of the cover manifold 902 are also shown.

The clamp cover 901 includes a first fastener 918 that is configured to engage a second fastener 920 of the clamp base 910. The first and second fasteners 918, 920 are sized and shaped to removably engage each other. In the illustrated embodiment, the first fastener 918 includes a latch, and the second fastener 920 includes a grip member 922. When the clamp cover 901 is closed, the grip member 922 is received within an opening of the latch. The grip member 922 is secured to a lever 924 and operably coupled to the latch button 904. When the latch button 904 is pressed, the lever 924 moves to release the latch and the clamp cover 901. The biasing member 916 may facilitate rotating the clamp cover 901 to an open position.

Figure 11:
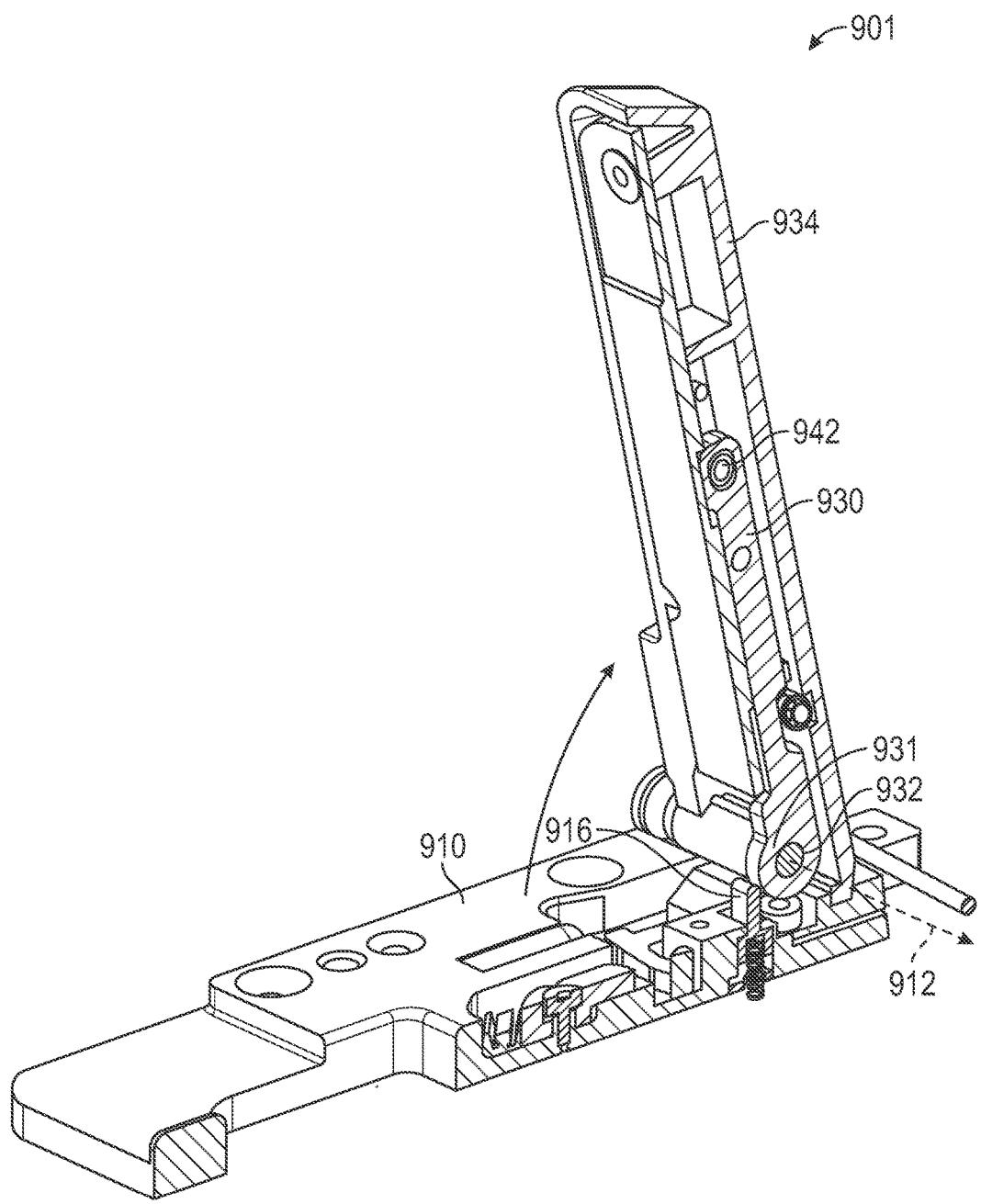
FIG. 11 illustrates a sectional view of a flow cell latch cover having a manifold arm in accordance with an embodiment.

FIG. 11 is a sectional view of a portion of the clamp cover 901. The clamp cover 901 includes a rotatable arm 930. The rotatable arm 930 has an arm hinge or base 931 that is rotably coupled to a pin or shaft 932 and is configured to rotate about the axis 912. The rotatable arm 930 is coupled to a body 934 of the clamp cover 901. For example, the rotatable arm 930 extends through a cavity of the body 934. The rotatable arm 930 is biased to rotate away from the clamp base 910 (as indicated by the arrow) by a biasing member 940 (e.g., spring) shown in FIG. 10. The rotatable arm 930 may be directly attached to the clamp manifold 902 (FIG. 10) at a joint 942. When the clamp manifold 902 engages the fluidic device, the rotatable arm 930 may be blocked from rotating further. The reaction force provided by the fluidic device to the clamp manifold 902 is also experienced by the rotatable arm 930 at the joint 942. As shown, the biasing member 916 is configured to engage the rotatable arm 930. The biasing member 916 may engage the rotatable arm 930 proximate to the arm hinge or base 931 of the rotatable arm 930.

Figure 12:
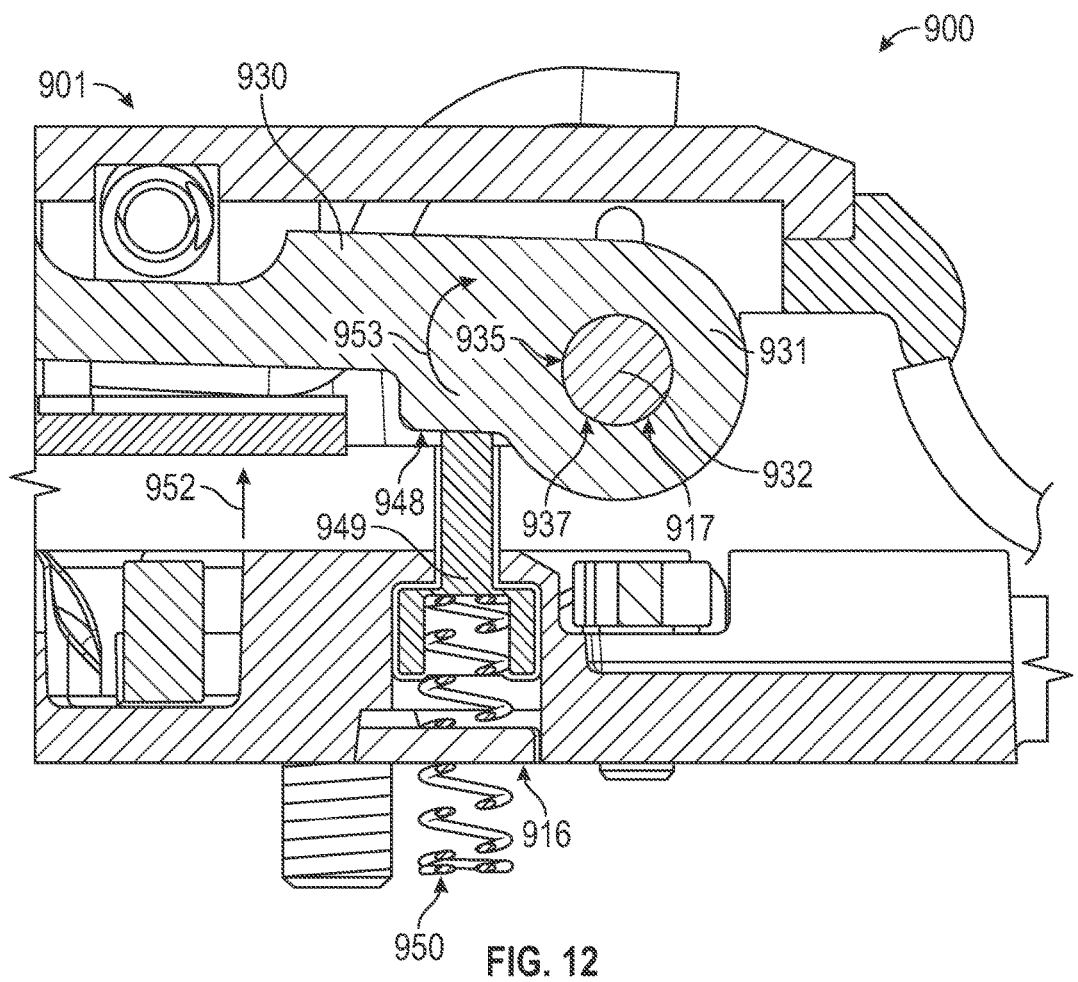
FIG. 12 is a cross-section of the flow cell latch clamp module of FIG. 10.

FIG. 12 is an enlarged cross-section of the FCLM 900. As shown, when the clamp cover 901 and the rotatable arm 930 are in the closed position, the biasing member 916 engages the rotatable arm 930 at an arm surface 948. The biasing member 916 includes a post 949 and a spring 950 that are configured to provide a biasing force 952. It should be understood, however, that other elements may be configured to provide a biasing force 952. In the illustrated embodiment, the biasing force 952 is a linear force (e.g., upward force) directly against the rotatable arm 930. The biasing member 940 provides a rotating force 953. The biasing force 952 is configured to press the rotatable arm 930 against the shaft 932.

Figure 13:
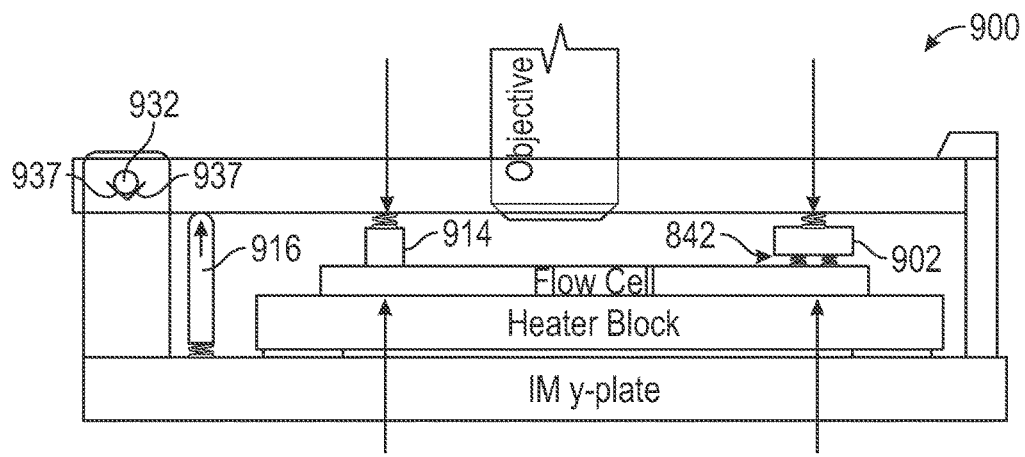
FIG. 13 is a schematic side view of the flow cell latch clamp module illustrating forces that are experienced by a flow cell in accordance with an embodiment.

The biasing force 952 may facilitate positioning the clamp manifold 902 relative to the fluidic device so that the ports 944, 946 and passages 844, 846 may be aligned and fluidically coupled. An opening 935 of the arm base 931 that receives the pin or shaft 932 may have a non-circular shape. More specifically, a pair of planar portions 937 of an interior surface of the arm base 931 are configured to engage and have the shaft 932 positioned therebetween. The arm surface 948 and the planar portions 937 are sized and shaped relative to each other to locate the manifold 902 at a designated position. The biasing force 952 provided by the biasing member 916 is configured such that the planar portions 937 engage the pin or shaft 932. In this manner, the clamp manifold 902 may be more precisely positioned. FIG. 13 illustrates the different forces experienced by the FCLM 900.

Figure 14:
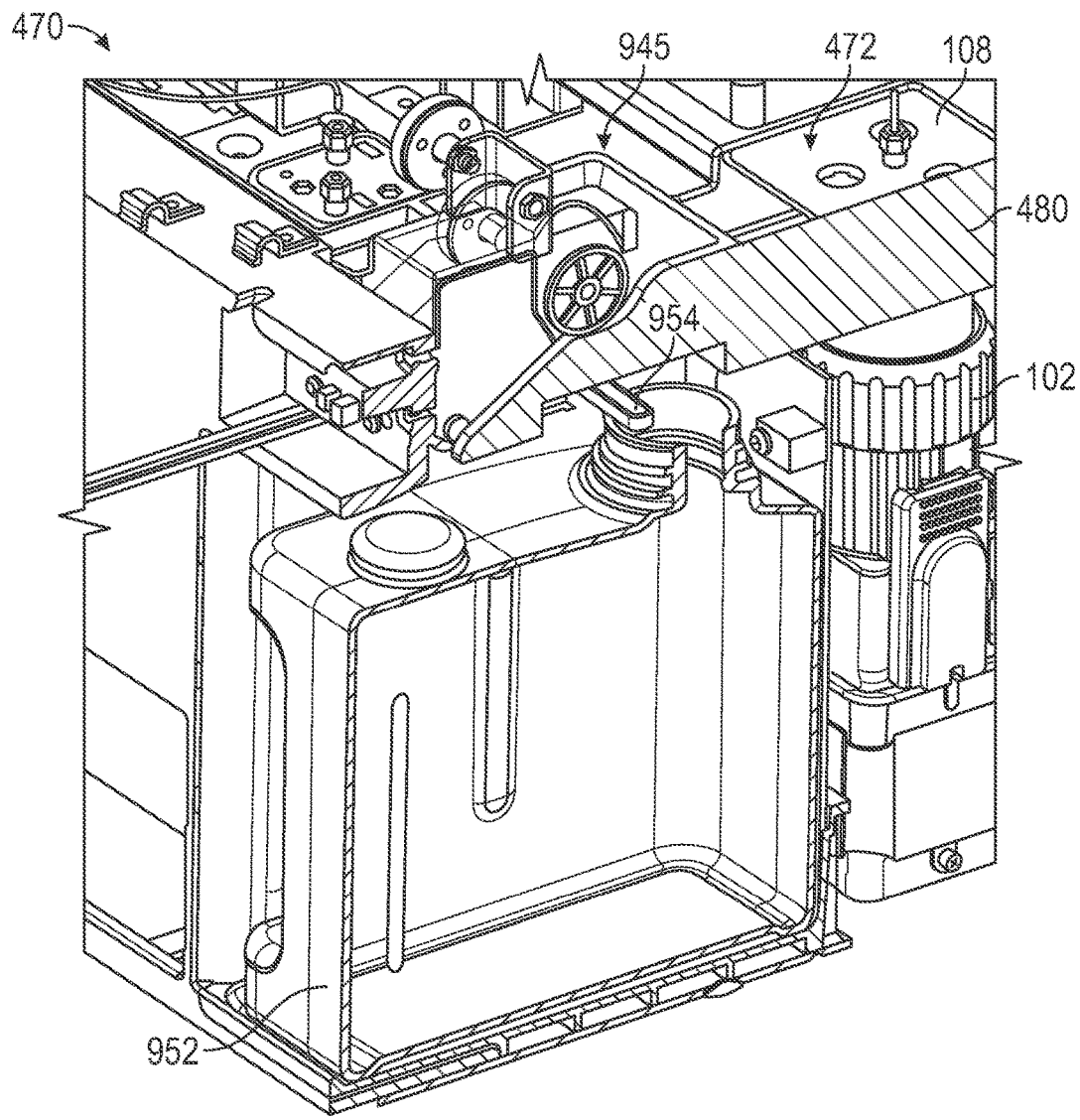
FIG. 14 is an enlarged sectional view of a portion of the fluidics automation module illustrating a locking mechanism in accordance with an embodiment.
Figure 15:
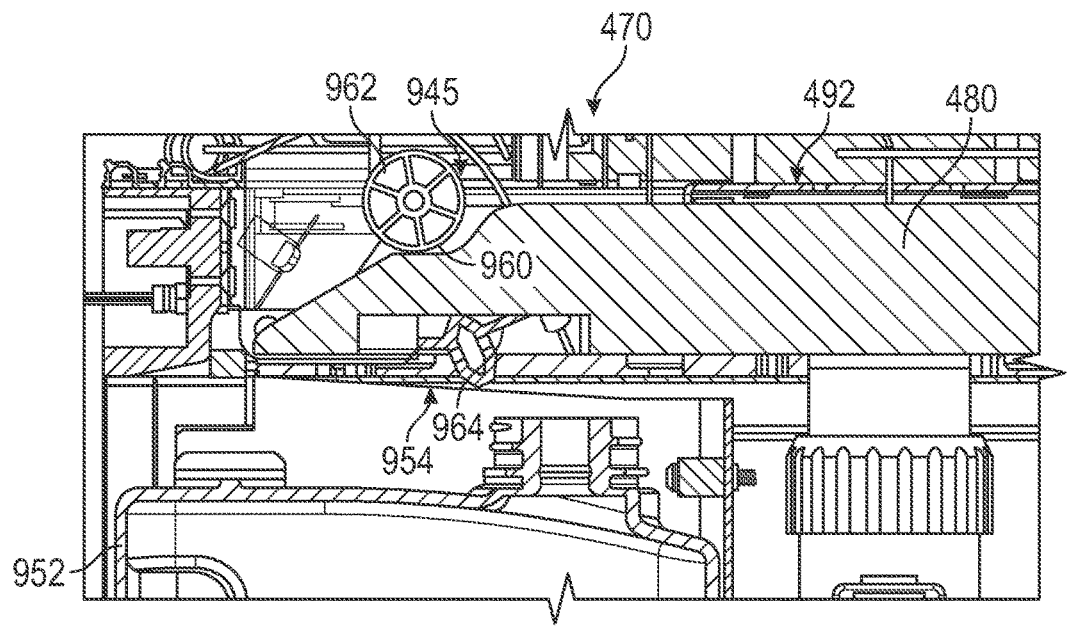
FIG. 15 is a side view of the locking mechanism of FIG. 14 in a locked position.
Figure 16:
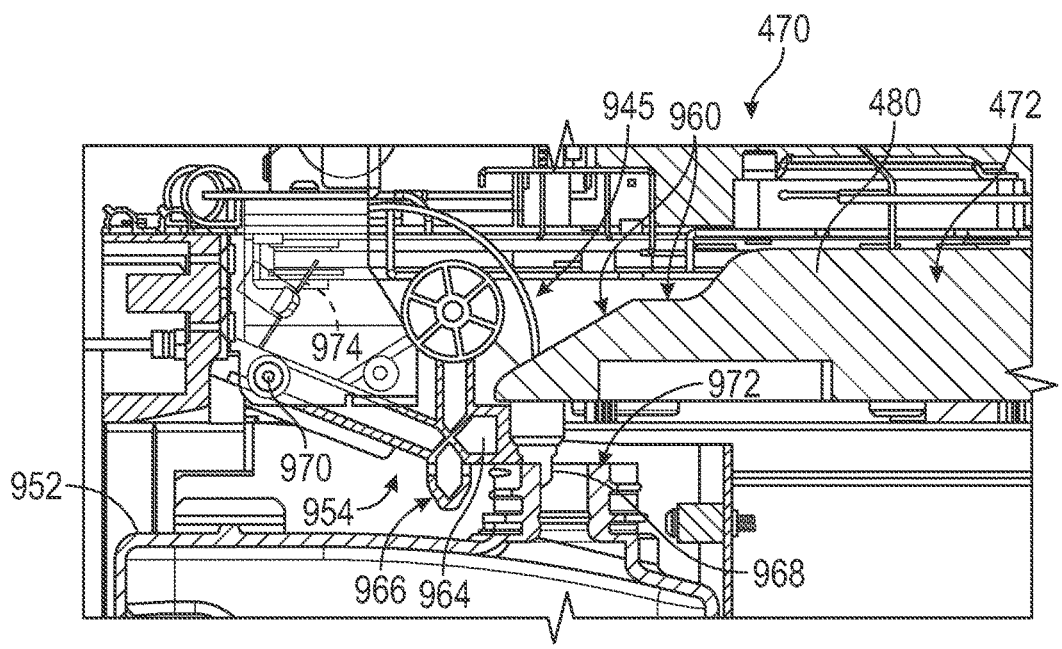
FIG. 16 is a side view of the locking mechanism of FIG. 14 in an unlocked position.

FIGS. 14-16 illustrate different views of a locking mechanism 945 of the FAM 470. The locking mechanism 945 includes a lock assembly 954 and the manifold assembly 472. In the illustrated embodiment, the manifold assembly 472 includes the manifold carriage 480, the manifold body 108, the valve 102, and the sipper tubes 103, 104 (FIG. 2A). However, the manifold assembly 472 may include fewer or more elements in other embodiments. The locking mechanism 945 is configured to impede (e.g., prevent) removal of a fluid container 952 during operation of the detection apparatus 1000. In particular embodiments, the locking mechanism 945 also positions a port for providing fluid into or out of the fluid container 952. In the illustrated embodiment, the fluid container 952 is configured to receive waste from the detection apparatus 1000. It is contemplated, however, that fluids may be drawn from the fluid container 952 in other embodiments.

FIG. 15 shows a side view of the locking mechanism 945 when the detection apparatus is in a user-loading position or user-unloading position. In either of the user-loading position or the user-unloading position, the fluid container 952 and the reagent cartridge 400 are permitted to be moved within the receptacle of the housing. FIG. 16 shows a side view of the locking mechanism 945 when the detection apparatus is operably connected to the reagent cartridge and/or the fluid container. When operably connected, fluid may be directed through the detection apparatus from the reagent cartridge, to the flow cell, and (optionally) into the fluid container 952. When operably connected, the fluid container 952 has an essentially fixed position such that the fluid container 952 may not be inadvertently removed during operation of the detection apparatus.

In the illustrated embodiment, the manifold assembly 472 is configured to engage the lock assembly 954. At the loading position shown in FIG. 15, the manifold carriage 480 is engaged with the lock assembly 954. The lock assembly 954 includes a roller 962 and a movable arm 964. The manifold carriage 480 includes a ramp surface 960 that is configured to engage the roller 962. When engaged, the roller 962 rests upon the ramp surface 960 and the movable arm 964 is positioned away from the fluid container 952. As such, the fluid container 952 is permitted to be loaded into the receptacle or removed from the receptacle (e.g., for emptying).

In FIG. 16, the manifold assembly 472 has been moved away from the lock assembly 954. The lock assembly 954 is permitted to rotate about an axis 970. In this position, the manifold body 108 is in fluid communication with reagent cartridge 400. For example, sequencing operations may be conducted when the manifold assembly 472 is positioned as shown in FIG. 16. The movable arm 964 includes a blocking surface 966 and a fluid port 968. The fluid port 968 is positioned within an opening 972 of the fluid container 952, and the blocking surface 966 is positioned to block the fluid container 952 should a person attempt to remove the fluid container 952 during operation of the detection apparatus.

Accordingly, the manifold carriage 480 is configured to move between an outward position (shown in FIG. 15) and an inward position (shown in FIG. 16). The movable arm 964 is configured to pivot downward with the assistance of a lock spring 974 when the roller 962 is disengaged from the surface 960. The waste port 968 lowers into the fluid container 952 as the roller moves down the surface 960. The blocking surface 966 is positioned to block a neck of the fluid container 952. This blockage will not allow a user to remove the fluid container 952 from the detection apparatus.

Figure 17A:
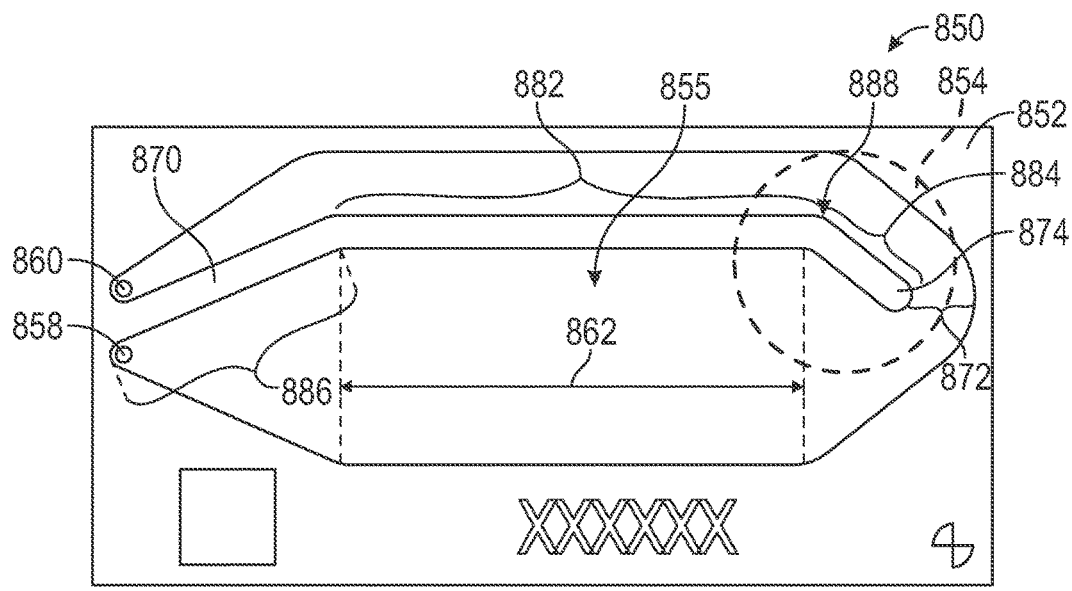
FIG. 17A is a plan view of a flow cell in accordance with an embodiment.
Figure 18:
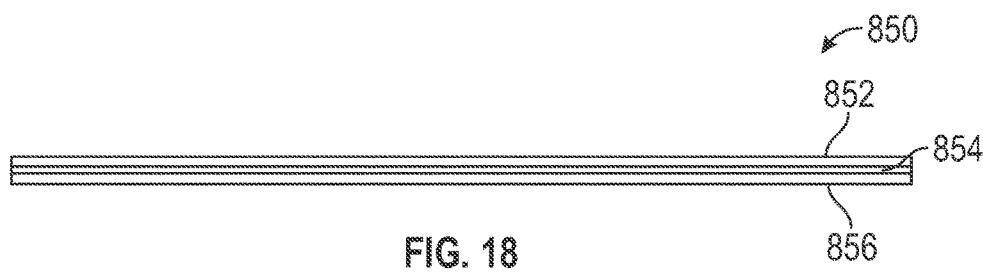
FIG. 18 is a side view of the flow cell of FIG. 17.

FIG. 17A is a plan view of the flow cell 850, and FIG. 18 is a side view of the flow cell 850. In the illustrated embodiment, the flow cell 850 includes a first substrate layer 852, an interposer layer 854, and a second substrate layer 856. The interposer layer 854 is sandwiched between the first and second substrate layers 852, 856. The flow cell 850 defines a flow channel 855 that extends between an inlet 858 and an outlet 860. The flow channel 856 defines an imaging region 862 in which an interior surface of the first substrate layer 852 and/or an interior surface of the second substrate layer 856 may be imaged by the microfluorometer. The flow channel 856 also includes an outlet region 863 that returns the fluid toward the manifold. The interposer layer 854 may be an inorganic solid. For example, the interposer layer 854 may be a polyimide layer (e.g., black Kapton). The first and second substrate layers 852, 856 may be an organic solid.

In particular embodiments, the flow cell 850 is manufactured through laser bonding (or laser welding) in which an interface between the inorganic solid and an organic solid is melted and allowed to solidify. A "substrate layer" is a layer that is capable of being coupled to other layers and laser welded (or laser bonded) to the other substrate layer. The substrate layers may include or be an inorganic solid or an organic solid. It should be understood that the term "substrate layer" is not limited to a single continuous body of the same material, unless otherwise explicitly stated. For example, a substrate layer may be formed form multiple sub-layers of the same or different materials. Moreover, each substrate layer may include one or more elements located therein that comprise different materials. For example, a substrate layer may include electrodes or conductive traces in addition to a base substrate material, such as glass or thermoplastic. Optionally, a substrate layer may be secured to other elements or components prior to the substrate layer being welded to another substrate layer.

An "inorganic solid" refers to a substrate having an internal microstructure held together by bonds between inorganic atoms. A trace or small amount of organic matter can occur in the internal microstructure of the inorganic solid so long as the structural integrity is primarily mediated by bonds and interactions between inorganic atoms. Examples of material for inorganic solid include, but are not limited to, glass and modified or functionalized glass, ceramics, silica or silica-based materials, including silicon and modified silicon, metals, and optical fiber bundles.

An "organic solid" refers to a substrate having an internal microstructure that is held together by bonding between organic atoms or molecules. A trace or small amount of inorganic matter can occur in the internal microstructure of the organic solid. Examples of material for organic solids include, but are not limited to, plastics, thermoplastics, thermosets, nylon, cyclic olefin copolymers (e.g. Zeonor), cyclic olefin polymers, carbon fiber, and polymers. Exemplary thermoplastics include polyacrylate, polyamide, polyimide (e.g. Kapton products from DuPont), polybutylene terephthalate, polycarbonate, polyether ketone, polyethylene, polyphenylene sulfide, polyacetal, polypropylene, polystyrene, polysulfone, polyvinyl butyral and polyvinyl chloride. Thermoplastics are particularly useful of which Kapton KJ and black Kapton KJ are examples A "radiation-absorbing material" is a material that absorbs radiation within a designated region or range of the electromagnetic spectrum. The radiation-absorbing material may be or may be part of a substrate layer that is secured to another substrate layer through laser-welding. Radiation-absorbing material may be in the form of organic solids, such as the organic solids described above. For example, polyimide film, such as a Kapton (DuPont) film, may absorb appreciably at wavelengths below 650 nm. A laser beam in which the light has a sufficient wavelength (e.g., 480 nm) may be directed to the polyimide polymers of the film. The polyimide polymers absorb and are melted by the light.

A substrate layer may be impregnated with a radiation-absorbing material. For example, an organic solid can be impregnated with a dye or with carbon black, as is the case for black Kapton (carbon black-impregnated polyimide available from DuPont). A dye that is used can be matched to a particular laser according to overlap between the wavelength emitted by the laser and the absorption spectrum for the dye. Black Kapton can be activated (e.g. via heating) by a laser that emits at 1064 nm.

An organic solid may be configured to absorb radiation in any of a variety of regions of the spectrum including for example in the UV (e.g. extreme UV or near UV), VIS (e.g. red, orange, yellow, green, blue, indigo or violet), or IR (e.g. near IR, mid IR or far IR) regions of the spectrum. It will be understood that an organic solid can be chosen based on absence of absorption in one or more of regions of the spectrum, including for example, one or more of the aforementioned regions. The inorganic solid may transmit radiation in at least part of the spectrum that is absorbed by the organic solid.

A "solid layer" refers to a substrate that is insoluble in aqueous liquid. The substrate can be non-porous or porous. The solid layer can be rigid or flexible. A nonporous solid is generally provides a seal against bulk flow of liquids or gases. Exemplary solids include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers. Particularly useful solid for some embodiments have at least one surface located within a flowcell apparatus.

Optionally, a chemically reactive layer (or sub-layer) may be present between two other layers during a bonding step. A "chemically reactive layer" refers to a surface coating or region between surfaces that contains at least one moiety that is capable of becoming covalently modified or covalently attached to at least one other moiety upon physical or chemical stimulation. In some embodiments, an interface can be occupied by a liquid, gas, solid, or plasma that contains the reactive moiety.

The chemically reactive layer can be a coating on either or both of the two other layers. Alternatively, the chemically reactive layer can be present in or on an intermediate material that is present between the two other layers such that the two other layers become attached via the intermediate material as a result of carrying out the fabrication method. Similarly, the chemically reactive layer can be a liquid layer containing cross-linking reagents that are reactive to, for example, both an organic layer and an inorganic layer.

A chemically reactive layer can be created on a solid layer using, for example, a silanization method. Techniques such as vapor phase deposition, dip coating, spin coating and spray coating can be used to silanize a surface. In some embodiments, such methods can be used to apply a silane coat across the entirety of a surface. However, it is also possible to create a silanization pattern on a surface, for example, using masking methods or precision spraying methods. For example, as set forth in further detail below it may be desirable to apply silane (or other chemically reactive moieties) selectively to regions on the surface of an inorganic layer that are to be bonded to an organic layer, while avoiding or minimizing silanization (or other chemical modification) of other regions of the inorganic layer where a bond to the organic layer is not wanted. If desired the surface of an organic layer can be patterned with silane or other chemically reactive coating using similar techniques.

Examples of silanes that can be used include, but are not limited to, acrylate functional silanes, aldehyde functional silanes, amino functional silanes, anhydride functional silanes, azide functional silanes, carboxylate functional silanes, phosphonate functional silanes, sulfonate functional silanes, epoxy functional silanes, ester functional silanes, vinyl functional silanes, olefin functional silanes, halogen functional silanes and dipodal silanes with any or none of the above functional groups. The choice of silane functionality can be made based on the reactivity of the organic material to which it will react. For example, amino functional silanes react with thermoplastics such as polyacrylate, polyamide, polyamide-imide, polybutylene terephthalate, polycarbonate, polyether ketone, polyethylene, polyphenylene sulfide, polysulfone, polyvinyl butyral and polyvinyl chloride. Vinyl and olefin functional silanes react with thermoplastics such as polyacetal, polyethylene, and polypropylene. Acrylate functional silanes react with thermoplastics such as polypropylene, and polystyrene.

In some embodiments, the interposer layer 854 defines the lateral boundaries of the flow channel 855. As shown, the flow channel 855 is defined by an elongated wall extension 870. The elongated wall extension 870 does not extend entirely cross the flow cell 850 such that a channel 872 exists between an end 874 of the elongated wall 870 and an outer portion of the interposer layer 854. The elongated wall 870 includes a first (or proximal) segment 880, a second (or intermediate) segment 882, and a third (or distal segment) 884. The proximal segment 880 is located proximate to the inlet 858 and outlet 860. The distal segment 884 extends from the intermediate segment 882 in a non-parallel direction with respect to the distal segment 884. As such, the intermediate segment 882 and the distal segment 884 form a bend or kink 888.

Figure 17B:
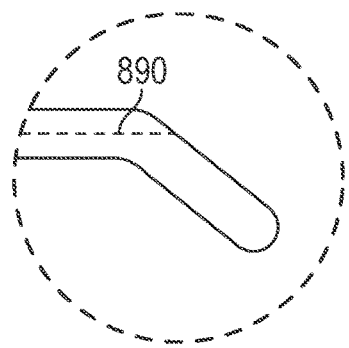
FIG. 17B illustrates a portion of an elongated wall of the flow cell of FIG. 17A in which an interposer layer is laser-bonded to a substrate layer using a first rastering pattern.

The flow call 850 may be manufactured in a manner that is similar to the multi-layer fluidic devices set forth in U.S. Patent Application Publication No. US 20160023208 A1, which is incorporated herein by reference in its entirety. For example, the interposer layer 854 is laser-bonded to the first substrate layer 852 and/or the second substrate layer 856 by directing a beam spot of a laser beam (not shown) along an interface between the interposer layer 854 and the corresponding substrate layer. The beam spot may be moved back-and-forth (or rastered) along the interface to form a series of weld lines. In some embodiments, the rastering of the beam spot along the intermediate segment 882 continues in the same direction along the distal segment 884 such that a single weld line 890 (FIG. 17B) may extend across the intermediate segment 882 and at least a portion of the distal segment 884. A plurality of the weld lines 890 may be provided in a series along the interface layer 854 such that the area of the interface is essentially covered by the weld lines 890. In other embodiments, however, the weld line 890 may extend parallel to the edges of the elongated wall extension 870. For example, the weld lines 890 may extend parallel to the edges of the intermediate segment 882 and then parallel to the edges of the distal segment 884.

Figure 17C:
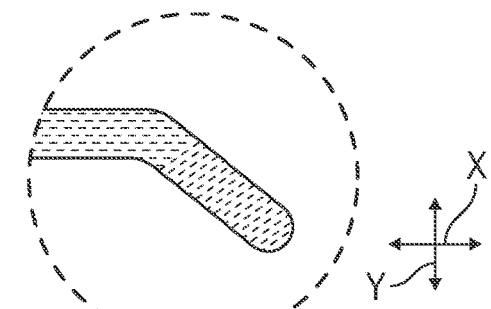
FIG. 17C illustrates a portion of an elongated wall of the flow cell of FIG. 17A in which an interposer layer is laser-bonded to a substrate layer using a second rastering pattern.

In other embodiments, however, the rastering along the interface of the distal segment 884 and the corresponding substrate layer may be in a direction that is not parallel to or does not coincide with the rastering along the intermediate layer 882. Alternatively or in addition to the non-parallel directions, the direction of the rastering may not be parallel to the edges of the elongated wall extension 870. An example is shown in FIG. 17C in which weld lines 891 along the intermediate segment 882 may be parallel to an X-axis (or parallel to the edges of the intermediate segment 882), but weld lines 892 along the distal segment 884 may be in a direction that has an X-component and a Y-component. The weld lines 892 may be non-orthogonal with respect to the edges of the distal segment 884. It is suspected that the non-parallel rastering along the distal segment 884 may reduce the likelihood of delamination of the distal segment 884 from other layers. In some embodiments, the different rastering patterns may be identified through inspection of the flow cell. For example, the flow cell may be diced to reveal a cross-section that extends through the intermediate segment 882 and a cross-section through the distal segment 884. Using a microscope (e.g., scanning electron microscope (SEM)), the cross-sectional surfaces may be examined to identify characteristics of the different segments.

In particular embodiments a fluidic system can be configured to allow re-use of one or more reagents. For example, the fluidic system can be configured to deliver a reagent to a flow cell, then remove the reagent from the flow cell, and then re-introduce the reagent to the flow cell. One configuration is exemplified in the apparatus and methods set forth in U.S. patent application Ser. No. 14/453,868 filed on Aug. 7, 2014 and entitled "FLUIDIC SYSTEM FOR REAGENT DELIVERY TO A FLOW CELL," the content of which is incorporated by reference in its entirety.

Embodiments of the present fluidic systems and methods find particular use for nucleic acid sequencing techniques. For example, sequencing-by-synthesis (SBS) protocols are particularly applicable. In SBS, extension of a nucleic acid primer along a nucleic acid template is monitored to determine the sequence of nucleotides in the template. The underlying chemical process can be polymerization (e.g. as catalyzed by a polymerase enzyme) or ligation (e.g. catalyzed by a ligase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates can be subjected to an SBS technique on a surface under conditions where events occurring for different templates can be distinguished. For example, the templates can be present on the surface of an array such that the different templates are spatially distinguishable from each other. Typically the templates occur at features each having multiple copies of the same template (sometimes called "clusters" or "colonies"). However, it is also possible to perform SBS on arrays where each feature has a single template molecule present, such that single template molecules are resolvable one from the other (sometimes called "single molecule arrays").

Flow cells provide a convenient substrate for housing an array of nucleic acids. Flow cells are convenient for sequencing techniques because the techniques typically involve repeated delivery of reagents in cycles. For example, to initiate a first SBS cycle, one or more labeled nucleotides, DNA polymerase, etc., can be flowed into/through a flow cell that houses an array of nucleic acid templates. Those features where primer extension causes a labeled nucleotide to be incorporated can be detected, for example, using methods or apparatus set forth herein. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary sequencing techniques are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

For the nucleotide delivery step of an SBS cycle, either a single type of nucleotide can be delivered at a time, or multiple different nucleotide types (e.g. A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, a microfluorometer or read head need only provide excitation at a single wavelength or in a single range of wavelengths. Thus, a microfluorometer or read head need only have a single excitation source and multiband filtration of excitation need not be necessary. For a nucleotide delivery configuration where delivery results in multiple different nucleotides being present in the flow cell at one time, features that incorporate different nucleotide types can be distinguished based on different fluorescent labels that are attached to respective nucleotide types in the mixture. For example, four different nucleotides can be used, each having one of four different fluorophores. In one embodiment the four different fluorophores can be distinguished using excitation in four different regions of the spectrum. For example, a microfluorometer or read head can include four different excitation radiation sources. Alternatively a read head can include fewer than four different excitation radiation sources but can utilize optical filtration of the excitation radiation from a single source to produce different ranges of excitation radiation at the flow cell.

In some embodiments, four different nucleotides can be detected in a sample (e.g. array of nucleic acid features) using fewer than four different colors. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detectable under particular conditions while a fourth nucleotides type lacks a label that is detectable under those conditions. In an SBS embodiment of the second example, incorporation of the first three nucleotide types into a nucleic acid can be determined based on the presence of their respective signals, and incorporation of the fourth nucleotide type into the nucleic acid can be determined based on absence of any signal. As a third example, one nucleotide type can be detected in two different images or in two different channels (e.g. a mix of two species having the same base but different labels can be used, or a single species having two labels can be used or a single species having a label that is detected in both channels can be used), whereas other nucleotide types are detected in no more than one of the images or channels. In this third example, comparison of the two images or two channels serves to distinguish the different nucleotide types.

The three exemplary configurations in the above paragraph are not mutually exclusive and can be used in various combinations. An exemplary embodiment is an SBS method that uses reversibly blocked nucleotides (rbNTPs) having fluorescent labels. In this format, four different nucleotide types can be delivered to an array of nucleic acid features that are to be sequenced and due to the reversible blocking groups one and only one incorporation event will occur at each feature. The nucleotides delivered to the array in this example can include a first nucleotide type that is detected in a first channel (e.g. rbATP having a label that is detected in the first channel when excited by a first excitation wavelength), a second nucleotide type that is detected in a second channel (e.g. rbCTP having a label that is detected in the second channel when excited by a second excitation wavelength), a third nucleotide type that is detected in both the first and the second channel (e.g. rbTTP having at least one label that is detected in both channels when excited by the first and/or second excitation wavelength) and a fourth nucleotide type that lacks a label that is detected in either channel (e.g. rbGTP having no extrinsic label).

Once the four nucleotide types have been contacted with the array in the above example, a detection procedure can be carried out, for example, to capture two images of the array. The images can be obtained in separate channels and can be obtained either simultaneously or sequentially. A first image obtained using the first excitation wavelength and emission in the first channel will show features that incorporated the first and/or third nucleotide type (e.g. A and/or T). A second image obtained using the second excitation wavelength and emission in the second channel will show features that incorporated the second and/or third nucleotide type (e.g. C and/or T). Unambiguous identification of the nucleotide type incorporated at each feature can be determined by comparing the two images to arrive at the following: features that show up only in the first channel incorporated the first nucleotide type (e.g. A), features that show up only in the second channel incorporated the second nucleotide type (e.g. C), features that show up in both channel incorporated the third nucleotide type (e.g. T) and features that don't show up in either channel incorporated the fourth nucleotide type (e.g. G). Note that the location of the features that incorporated G in this example can be determined from other cycles (where at least one of the other three nucleotide types is incorporated). Exemplary apparatus and methods for distinguishing four different nucleotides using detection of fewer than four colors are described for example in US Pat. App. Ser. No. 61/538,294, which is incorporated herein by reference.

In some embodiments, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; US 2002/0055100; U.S. Pat. No. 7,115,400; US 2004/0096853; US 2004/0002090; US 2007/0128624; or US 2008/0009420, each of which is incorporated herein by reference. Another useful method for amplifying nucleic acids on a surface is rolling circle amplification (RCA), for example, as described in Lizardi et al., *Nat. Genet.* 19:225-232 (1998) and US 2007/0099208 A1, each of which is incorporated herein by reference. Emulsion PCR on beads can also be used, for example as described in Dressman et al., *Proc. Natl. Acad. Sci. USA* 100:8817-8822 (2003), WO 05/010145, US 2005/0130173 or US 2005/0064460, each of which is incorporated herein by reference.

As set forth above, sequencing embodiments are an example of a repetitive process. The methods of the present disclosure are well suited to repetitive processes. Some embodiments are set forth below and elsewhere herein.

Accordingly, provided herein are sequencing methods that include (a) providing a fluidic system comprising (i) a flow cell comprising an optically transparent surface, (ii) a nucleic acid sample, (iii) a plurality of reagents for a sequencing reaction, and (iv) a fluidic system for delivering the reagents to the flow cell; (b) providing a detection apparatus comprising (i) a plurality of microfluorometers, wherein each of the microfluorometers comprises an objective configured for wide-field image detection in an image plane in x and y dimensions, and (ii) a sample stage; and (c) carrying out fluidic operations of a nucleic acid sequencing procedure in the cartridge and detection operations of the nucleic acid sequencing procedure in the detection apparatus, wherein (i) the reagents are delivered to the flow cell by the fluidic system, (ii) wide-field images of the nucleic acid features are detected by the plurality of microfluorometers, and (iii) at least some reagents are removed from the flow cell to a cache reservoir.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:
1. A detection apparatus, comprising:
a microfluorometer comprising an objective, an excitation radiation source, and a detector, the microfluorometer configured for wide-field image detection;
a fluidic system for delivering reagents from a reagent cartridge to a flow cell, the fluidic system comprising:
a manifold body having a plurality of fluidic channels configured for fluid communication between the reagent cartridge and an inlet of the flow cell;
a plurality of reagent sippers extending downward from ports in the manifold body, each of the reagent sippers configured to be placed into a reagent reservoir of the reagent cartridge so that liquid reagent can be drawn from the reagent reservoir into the reagent sipper; and
a valve configured to mediate fluid communication between the reagent reservoirs and the inlet of the flow cell, the fluidic channels fluidly connecting the plurality reagent sippers to the valve; and
a flow cell latch clamp module, comprising:
a clamp base;
a clamp cover for holding the flow cell, the clamp cover rotatably coupled to the clamp base, the clamp cover comprising a rotatable arm and a clamp manifold, wherein the rotatable arm extends through a cavity of a body of the clamp cover, and wherein the rotatable arm is directly connected to the clamp manifold, the clamp manifold having at least one port configured to be in flow communication with the flow cell;
a first biasing member that provides a rotating force for rotating the rotatable arm away from the clamp base; and
a second biasing member, the second biasing member engaging the rotatable arm to facilitate locating the clamp manifold,
wherein the objective is configured to direct excitation radiation from the radiation source to the flow cell and to direct emission from the flow cell to the detector, and wherein the microfluorometer is movable to acquire wide-field images of different areas of an inner surface of the flow cell.

2. The detection apparatus of claim 1, wherein the detection apparatus comprises no more than a single microfluorometer, the microfluorometer being an integrated microfluorometer having an epifluorescent detection configuration, the microfluorometer being movable relative to the flow cell latch clamp module.

3. The detection apparatus of claim 1, wherein a field diameter for the microfluorometer is at least 0.5 millimeters (mm) but no larger than 5 mm and a numerical aperture for the microfluorometer is at least 0.2 but no greater than 0.8.

4. The detection apparatus of claim 1, further comprising a fluidics automation module including a lift assembly for raising and lowering the reagent cartridge.

5. The detection apparatus of claim 1, further comprising a fluidics automation module including a belt assembly that moves the reagent cartridge during loading.

6. The detection apparatus of claim 1, wherein the fluidic channels are housed entirely within the manifold body.

7. The detection apparatus of claim 6, wherein the manifold body is formed from multiple layers of solid material bonded together.

8. The detection apparatus of claim 6, wherein the manifold body has a single layer of fluidic channels.

9. The detection apparatus of claim 1, wherein the valve is configured with inlet ports that correspond to each of the ports of the fluidic channels and configured with a single common outlet port which fluidly connects to the flow cell.

10. The detection apparatus of claim 1, wherein the fluidic system has no more than one valve that mediates fluid communication between the reagent reservoirs and the flow cell.

11. The detection apparatus of claim 1, further comprising an X-motor, a Y-motor, an X-stage, and a Y-stage, the X-motor and the Y-motor configured to move the X-stage and the Y-stage, respectively, in perpendicular directions with respect to each other, the microfluorometer being secured to the X-stage, the flow cell latch clamp module being secured to the Y-stage.

12. The detection apparatus of claim 1, wherein the rotatable arm includes an arm base that is rotatably coupled to a shaft of the flow cell latch clamp module, the second biasing member providing a linear force that is proximate to the arm base, the linear force pressing surfaces of the rotatable arm against surfaces of the shaft.

13. A detection apparatus, comprising:
a microfluorometer comprising an objective, an excitation radiation source, and a detector, the microfluorometer configured for wide-field image detection;
a fluidic system for delivering reagents from a reagent cartridge to a flow cell, the fluidic system comprising:
a manifold body having a plurality of fluidic channels configured for fluid communication between the reagent cartridge and an inlet of the flow cell;
a plurality of reagent sippers extending downward from ports in the manifold body, each of the reagent sippers configured to be placed into a reagent reservoir of the reagent cartridge so that liquid reagent can be drawn from the reagent reservoir into the reagent sipper; and
a valve configured to mediate fluid communication between the reagent reservoirs and the inlet of the flow cell, the fluidic channels fluidly connecting the plurality reagent sippers to the valve;
a flow cell latch clamp module having a clamp cover for holding the flow cell; and
a locking mechanism that includes a lock assembly and a manifold assembly, the manifold assembly including the manifold body and being configured to engage the lock assembly to release a fluid container from an operating position, the lock assembly including a fluid port that is in configured to be in fluid communication with the fluid container when the fluid container is held in the operating position, the fluid port being fluidly disconnected with respect to the fluid container when the lock assembly is engaged by the manifold assembly,
wherein the objective is configured to direct excitation radiation from the radiation source to the flow cell and to direct emission from the flow cell to the detector, and wherein the microfluorometer is movable to acquire wide-field images of different areas of an inner surface of the flow cell.

14. The detection apparatus of claim 13, wherein the manifold assembly includes a manifold carriage, the manifold carriage holding the manifold body, the manifold carriage configured to move with respect to the lock assembly and engage the lock assembly.

15. The detection apparatus of claim 14, wherein the lock assembly includes a roller that engages a ramp surface of the manifold carriage.

16. A sequencing system configured to perform a sequencing-by-synthesis protocol that includes the detection apparatus of claim 1 and the reagent cartridge of claim 1, the reagent cartridge having the reagent reservoirs, wherein the reagent reservoirs include sequencing reagents.

17. The sequencing system of claim 16, wherein at least one of the reagent reservoirs include a nucleic acid sample.

* * * * *

UNITED STATES PATENT AND TRADEMARK OFFICE
CERTIFICATE OF CORRECTION

PATENT NO. : 9,958,465 B2
APPLICATION NO. : 15/403896
DATED : May 1, 2018
INVENTOR(S) : Beng Keong Ang et al.

Page 1 of 1

It is certified that error appears in the above-identified patent and that said Letters Patent is hereby corrected as shown below:

On the Title Page

In Column 1 (*), Line 3, delete "days. days." and insert -- days. --, therefor.

In the Claims

In Column 32, Line 17, in Claim 13, before "configured" delete "in.".

Signed and Sealed this
Tenth Day of July, 2018

Andrei Iancu
*Director of the United States Patent and Trademark Office*